United States Patent [19]

Srinivasan et al.

[11] Patent Number: 5,792,331
[45] Date of Patent: Aug. 11, 1998

[54] PREFORMED POLYMER COATING PROCESS AND PRODUCT

[75] Inventors: Kannan Srinivasan, Sunnyvale; Neboisa Avdalovic, San Jose; Christopher A. Pohl, Union City, all of Calif.

[73] Assignee: Dionex Corporation, Sunnyvale, Calif.

[21] Appl. No.: 770,628

[22] Filed: Dec. 19, 1996

[51] Int. Cl.$^6$ .......................... G01N 27/26; G01N 27/447
[52] U.S. Cl. ............................................ 204/454; 427/407.2
[58] Field of Search ........................... 204/454; 427/407.2

[56] References Cited

U.S. PATENT DOCUMENTS

| | | | |
|---|---|---|---|
| 3,728,145 | 4/1973 | Hjerten | 117/54 |
| 3,935,340 | 1/1976 | Yamaguchi et al. | 427/216 |
| 4,137,367 | 1/1979 | Sample, Jr. et al. | 428/443 |
| 4,306,045 | 12/1981 | Yoshida et al. | 526/93 |
| 4,454,234 | 6/1984 | Czerlinski | 436/526 |
| 4,495,245 | 1/1985 | Zunker | 428/403 |
| 4,554,088 | 11/1985 | Whitehead et al. | 252/62.54 |
| 4,680,201 | 7/1987 | Hjerten | 427/230 |
| 4,690,749 | 9/1987 | Van Alstine et al. | 204/299 |
| 4,865,706 | 9/1989 | Karger et al. | 204/182.8 |
| 4,931,328 | 6/1990 | Swedberg | 428/36.91 |
| 4,997,537 | 3/1991 | Karger et al. | 204/182.8 |
| 5,017,540 | 5/1991 | Sandoval et al. | 502/158 |
| 5,074,982 | 12/1991 | Novotny et al. | 204/182.8 |
| 5,089,106 | 2/1992 | Karger et al. | 204/299 R |
| 5,221,447 | 6/1993 | Hjerten | 204/180.1 |
| 5,322,608 | 6/1994 | Karger | 204/299 R |
| 5,447,617 | 9/1995 | Shieh | 204/299 R |
| 5,605,613 | 2/1997 | Shieh | 204/451 |

FOREIGN PATENT DOCUMENTS

| | | |
|---|---|---|
| 0 442 177 | 2/1990 | European Pat. Off. |
| 91/11709 | 8/1991 | WIPO . |

OTHER PUBLICATIONS

Haaf et al., "Polymers of N-vinylpyrrolidone: Synthesis, Characterization and Uses," *Polymer Journal*, 17(1):143-152 (1985).

Anderson et al., "Crosslinking Aqueous Poly(vinyl pyrrolidone) Solutions by Persulfate," *Journal of Applied Polymer Science*, 23:2453-2462 (1979).

Henglein, A., "Crosslinking of Polymers in Solution Under the Influence of Y-Radiation," 63:1852-1858 (1959).

McCormick, R.M., "Cappillary Zone Electrophoretic Separation of Peptides and Proteins Using Low pH Buffers in Modified Silica Capillaries," *Anal. Chem.* 60:2322-2328 (1988).

Lauer et al., "Capillary Zone electrophoresis of Proteins in Untreated Fused Silica Tubing", *Anal. Chem.* 58:166-170 (1986).

*Encyclopedia of Polymer Science and Engineering*, (eds. Herman, H.F., et al.) John Wiley & Sons, New York, 15:183 (1990).

Gordon et al., "Rotocol for Resolving Protein Mixtures in Capillary Zone Electrophoresis," *Anal. Chem.* 63:69-72 (1991).

(List continued on next page.)

*Primary Examiner*—Erma Camperon
*Attorney, Agent, or Firm*—David J. Brezner

[57] ABSTRACT

A method of coating a solid support (e.g. a capillary or chromatography packing) to alter the properties of the support surface for separating components in a fluid stream. The method comprises (a) covalently binding a coupling agent (including functional groups capable of forming free radical sites under hydrogen abstraction conditions) to the support surface in a uniform layer, and (b) thereafter, contacting the bound coupling agent with a solution of preformed polymer comprising totally saturated carbon chain backbones including leaving groups, under hydrogen abstraction conditions of elevated temperature in the presence of a free radical catalyst to remove leaving groups from the carbon chains to form free radical carbon binding sites which covalently bond to the coupling agent layer and to crosslink at least some of the preformed polymer through the free radical carbon binding sites to form a dimensional polymer network coating on said solid support surface. Alternatively, the coating is applied directly to an organic solid support without an intermediate coupling agent.

25 Claims, 7 Drawing Sheets

OTHER PUBLICATIONS

Bushey et al., "Capillary Electrophoresis of Proteins in Buffers Containing High Concentrations of Zwitterionic Salts," *J. Chromatogr.* 480:301–310 (1989).

Stover et al., "Capillary Zone Electrophoresis of Histidine–Containing Compounds," *J. Chromatogr.* 470:241–250 (1989).

Gilges et al., "Capillary Zone Electrophoresis Separation of Basic and Acidic Proteins Using Poly(vinyl alcohol) Coatings in Fused Silica Capillaries," *Anal. Chem.* 66:2038–2046 (1994).

Hjerten, S., "High–Performance Electrophoresis Eliminatio of Electroendosmosis and Solute Adsorption," *Chromatogr.* 347:191–198 (1985).

Strege et al., "Capillary Electrophoretic Protein Separations in Polyacrylamide–Coated Silica Capillaries and Buffers Containing Ionic Surfactants," *J. Chromatogr.* 630:337–344 (1993).

Cifuentes et al., "Separation of Basic Proteins by Capillary Electrophoresis Using Cross–Linked Polyacrylamide–Coated Capillaries and Cationic Buffer Additives," *J. Chromatogr.* 665:63–72 (1993).

Herren et al., "Control of Electorosmosis in Coated Quartz Capillaries," *J. Celloid Interface Sci.*, pp. 46–55 (1987).

Yalpani et al., "Selective Chemical Modifications of Dextran," *J. Polymer Sci.*, 23:1395–1405 (1985).

Harris et al., "Synthesis and Characterization of Poly(ethylene Glycol) Derivatives," *J. Polymer Sci.*, 22:341–352 (1984).

Hjerten et al., "A New Type of pH–and Detergent–Stable Coating for Elimination of Electroendosomosis and Adsorption in (Capillary) Electrophoresis," *Electrophoresis*, 14:390–395 (1993).

Malik et al., "Simple Method for the Preparation of Highly Efficient Polymer–Coated Capillary Electrophoresis Columns," *J. Microcol.* 5:119–125 (1993).

Zhao et al., "Solute Adsorption on Polymer–Coated Fused–Silica Capillary Electrophoresis Columns Using Selected Protein and Peptide Standards," *Anal. Chem.* 65:2747–2752 (1993).

Cobb et al., "Electrophoretic Separations of Proteins in Capillaries with Hydrolytically Stable Surface Structures," *Anal. Chem.* 2478–2483 (1990).

Chiari et al., "Capillary Electrophoretic Separation of Proteins Using Stable, Hydrophilic Poly(acryloylaminoethoxyethanol)–Coated Columns," *J. Chromatogr.* 717:1–13 (1995).

Smith et al., "Capillary Zone Electrophoresis of Biological Substances with Fused Silica Capillaries Having Zero or Constant electroosmotic Flow," *Electrophoresis* 14:396–406 (1993).

Huang et al., "Hydrolytically Stable Cellulose–Derivative Coating for Capillary lectrophoresis of Peptides, Proteins and glycoconjugates," *Electrophoresis* 16:396–401 (1995).

Schmalzing et al., "Characterization and Performance of a Neutral Hydrophilic Coating for the Capillary Electrophoretic Separation of Biopolymers," *J. Chromatogr.* A652:149–159 (1993).

Odian, G., *Principles of Polymerization*, John Wiley & Sons, New York, pp. 249–255 (1991).

Henglein, A., "Crosslinking of Polymers in Solution Under the Influence of Y–Radiation," *J. Phys. Chem.*, 63:1852–1858 (1959).

*Acrylamide Polymerization — A Practical Approach*, Biorad Bulletin 1156, p.3 (1987).

Lenz, R.W., "Graft Polymer Formation," *Organic Chemistry of Synthetic High Polymers*, John Wiley & Sons: New York, pp. 711–713 (1967).

Lenz, R.W., "Allylic Abstraction Reactions," *Organic Chemistry of Synthetic High Polymers*, John Wiley & Sons: New York, pp. 292–293 (1967).

Greene et al., *Protective Groups in Organic Synthesis*, ((2nd ed.) (Eds: Green, T.W. and P.G.M. Wuts) John Wiley & Sons: New York, pp. 68–86 (1991).

Jong et al., "Determination of Milk Proteins by Capillary Electrophoresis," *J. Chromatogr.* A652:207–213 (1993).

Chen et al., "Capillary Electrophoresis — A New Clinical Tool," *Clin. Chem.*,37:14–19 (1991).

Matyska et al., "Synthesis and Characterization of Titania–Based Stationary Phases for HPLC," 20th International Symposium on HPL phase Separation and Related Techniques, San Francisco, California (Jun. 16–21 1996).

Pesek et al., "New Alumina–Based Stationary Phases for High–Performance Liquid Chromatogrpahy," *Journal of Chromatography*, 630:95–103 (1993).

Schomburg, G., "Polymers Coating of Surfaces in Column Liquid Chromatography and Capillary Electrophoresis," *Trends in Analytical Chemistry*, 10(5):163–169 (1991).

Kohler et al., "Stationary Phases in High Performance Liquid Chromatography: Chemical Modification by Polymer Coating," *LC–GC* 6(1):36–50 (1988).

Kohler, J., "Poly(vinylpyrrolidone)–Coated Silica: A Versatile, Polar Stationary Phase for HPLC," *Chromatographia* 21 (10):573–582 (1986).

Lenz et al., "Radical Abstraction Reactions," *Organic Chemistry of Synthetic High Polymers*, John Wiley & Sons: New York, pp. 288–289 (1967).

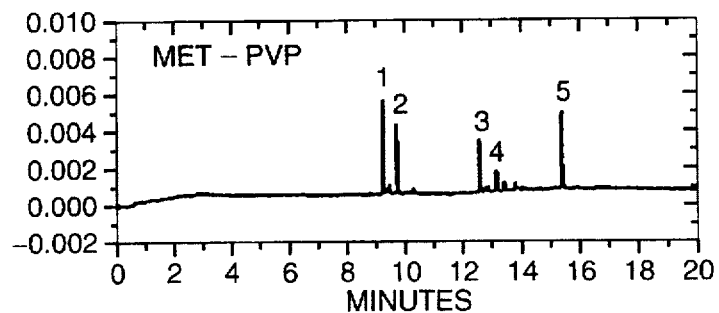
FIG._1A
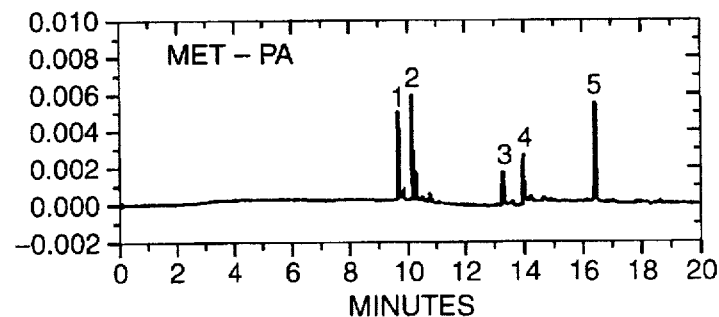
FIG._1B
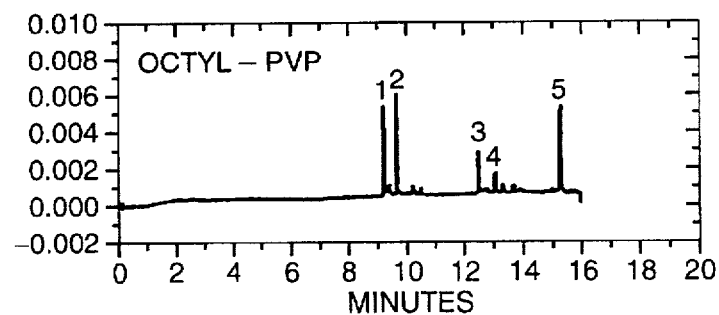
FIG._1C
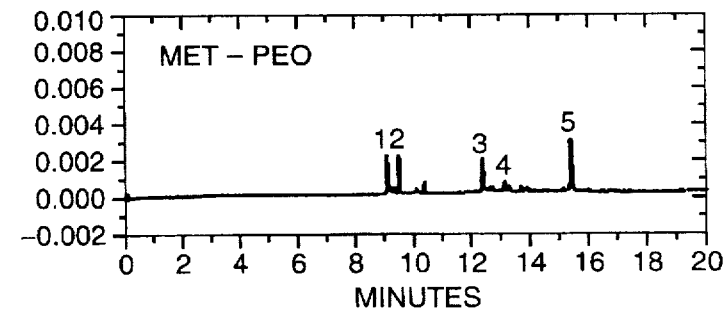
FIG._1D
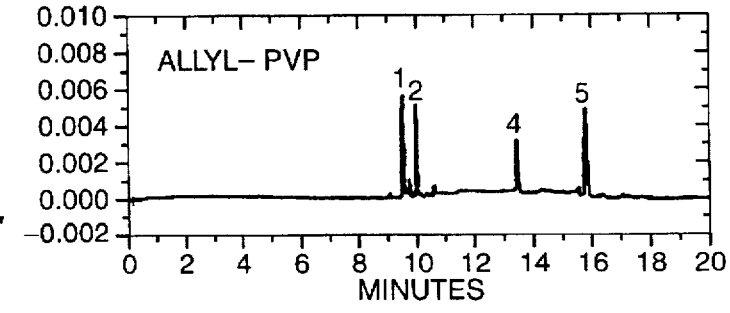
FIG._1E

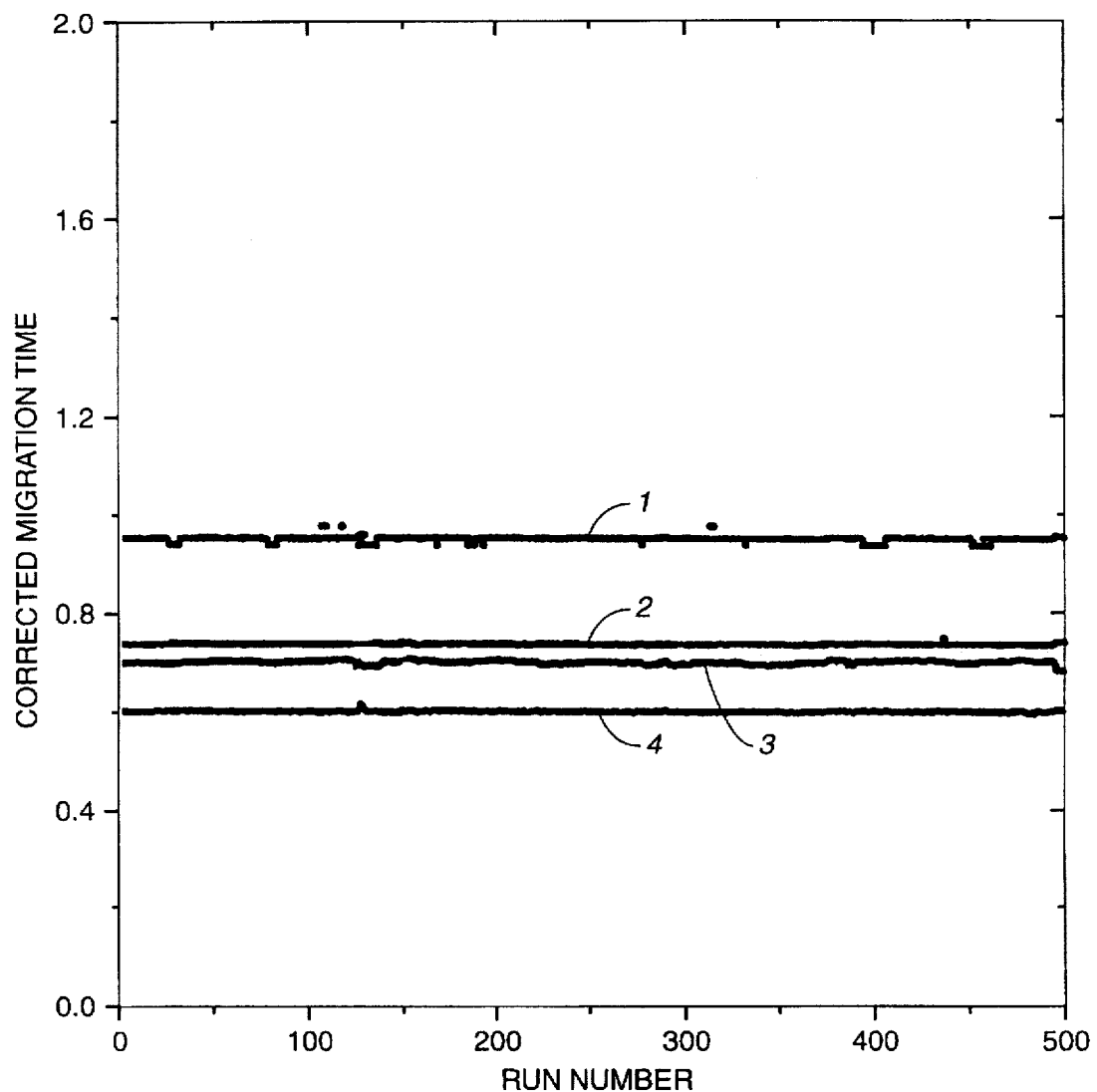
FIG._2

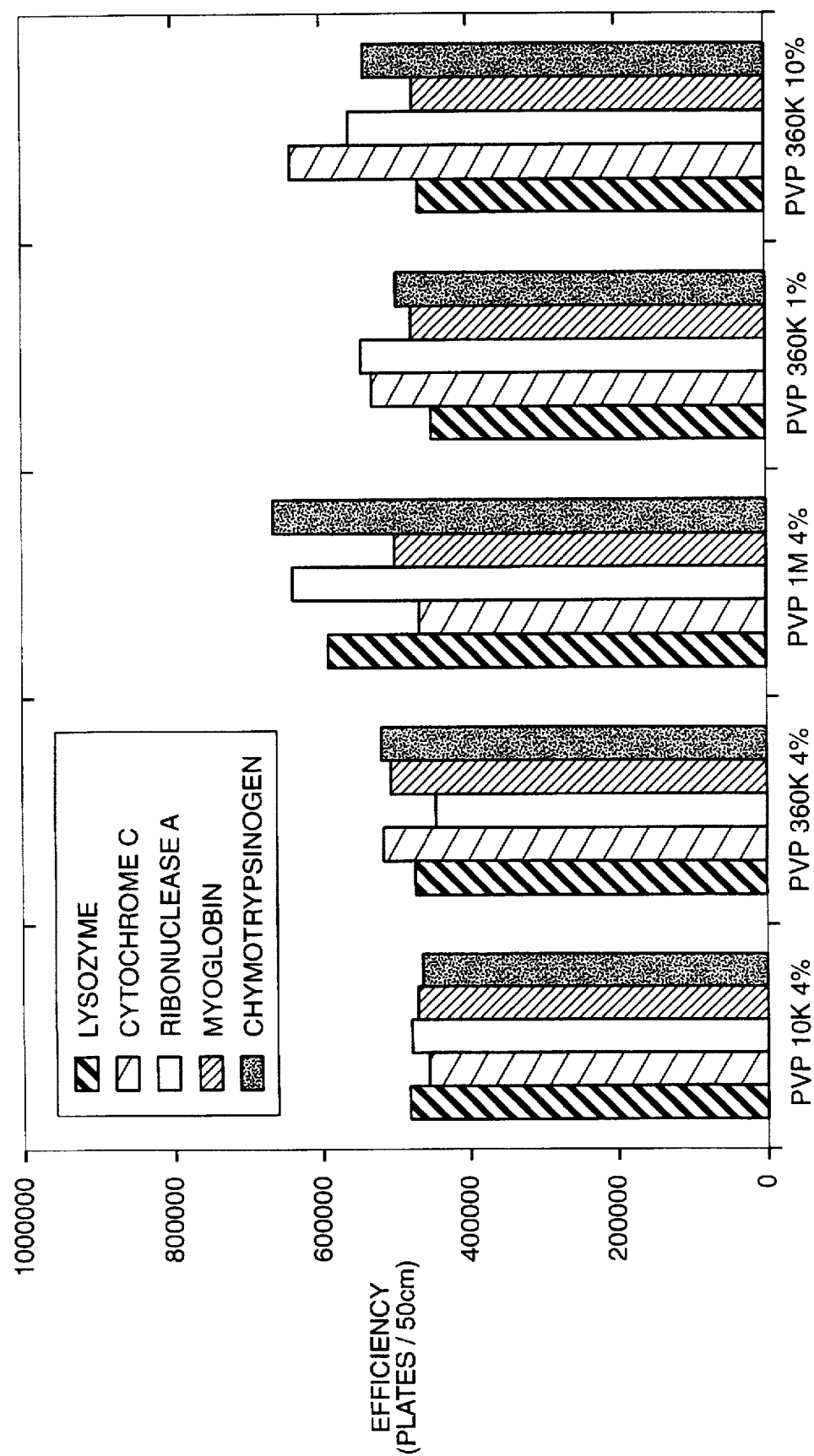
FIG._3

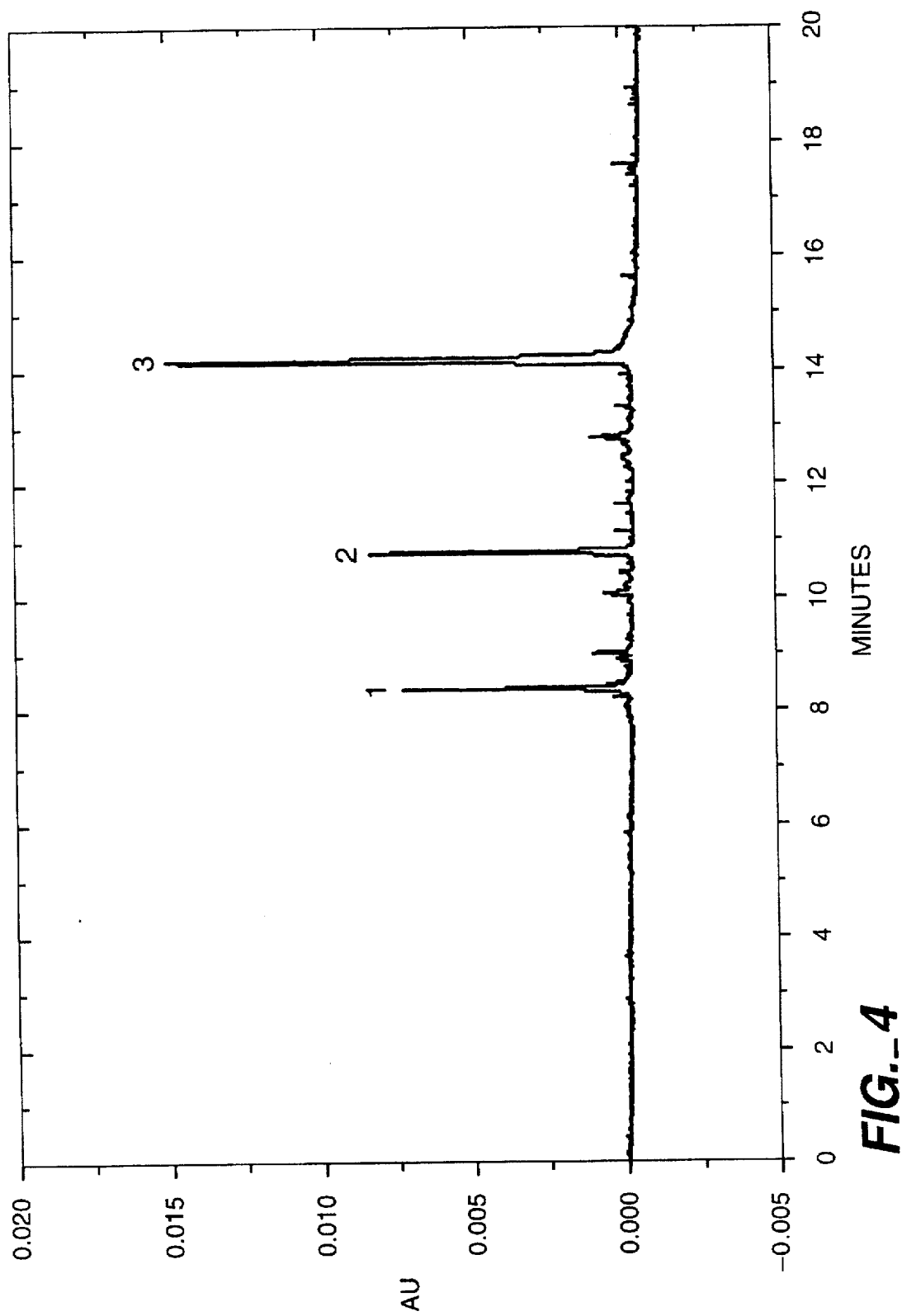
FIG._4

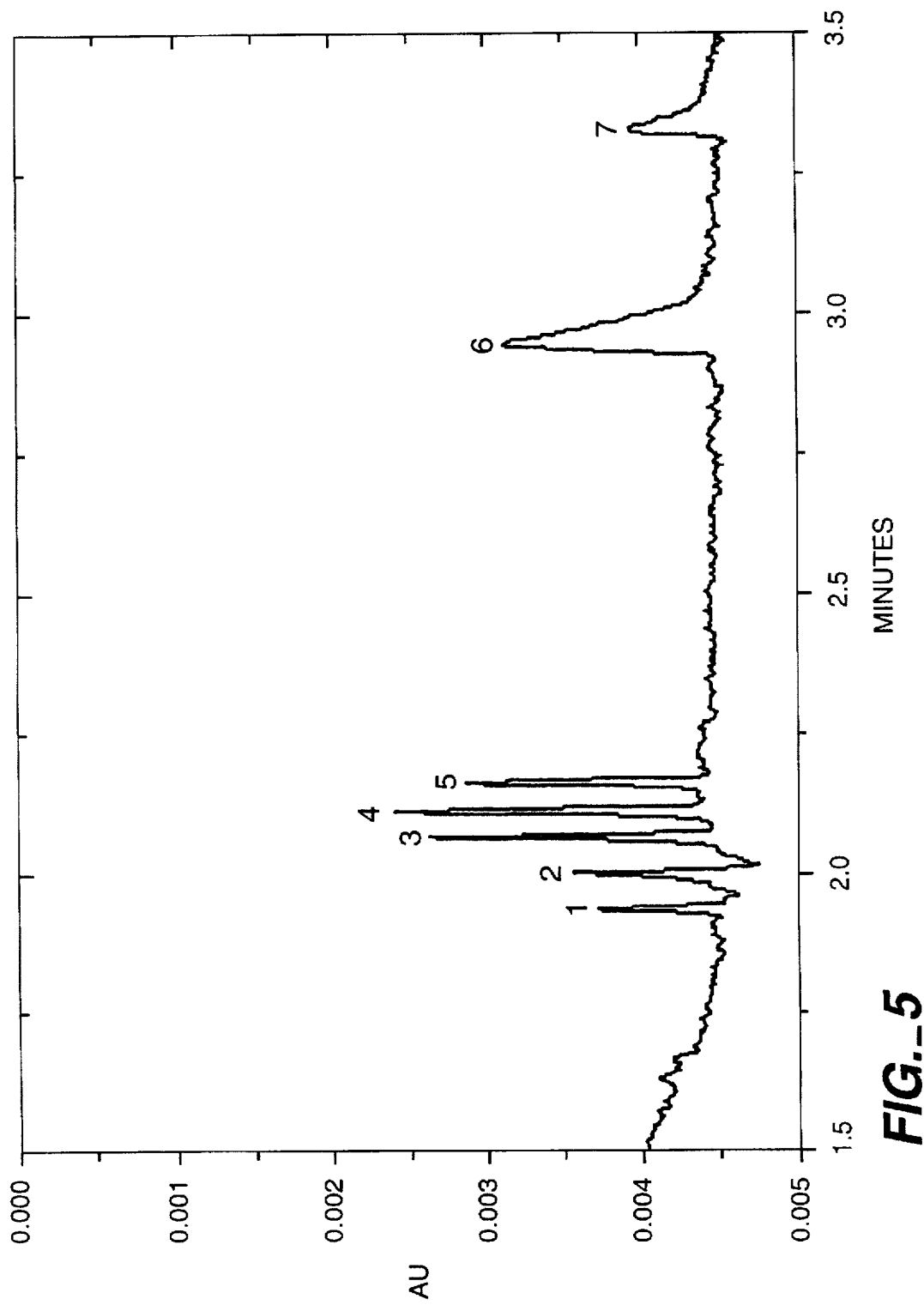
FIG._5

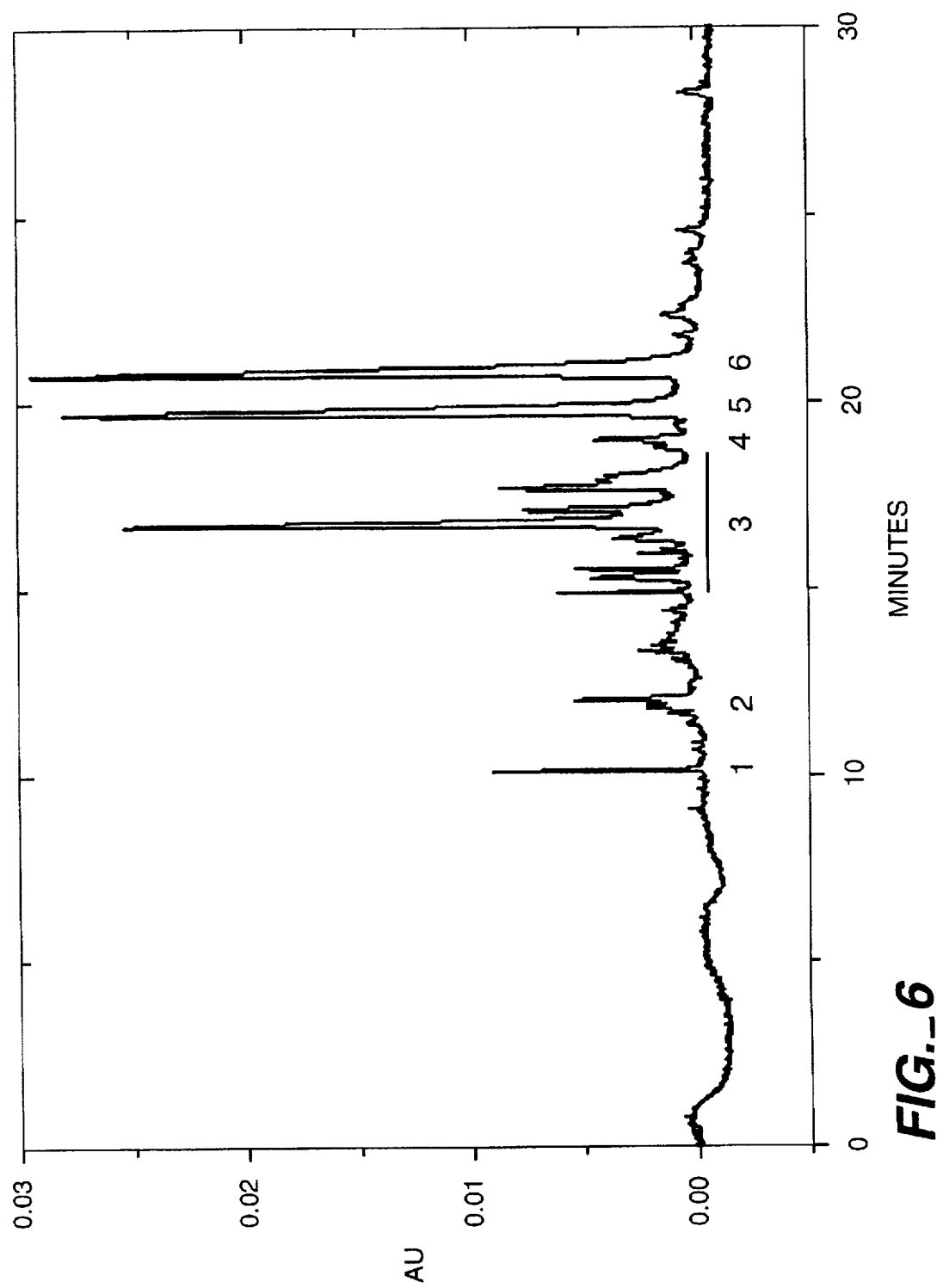
FIG._6

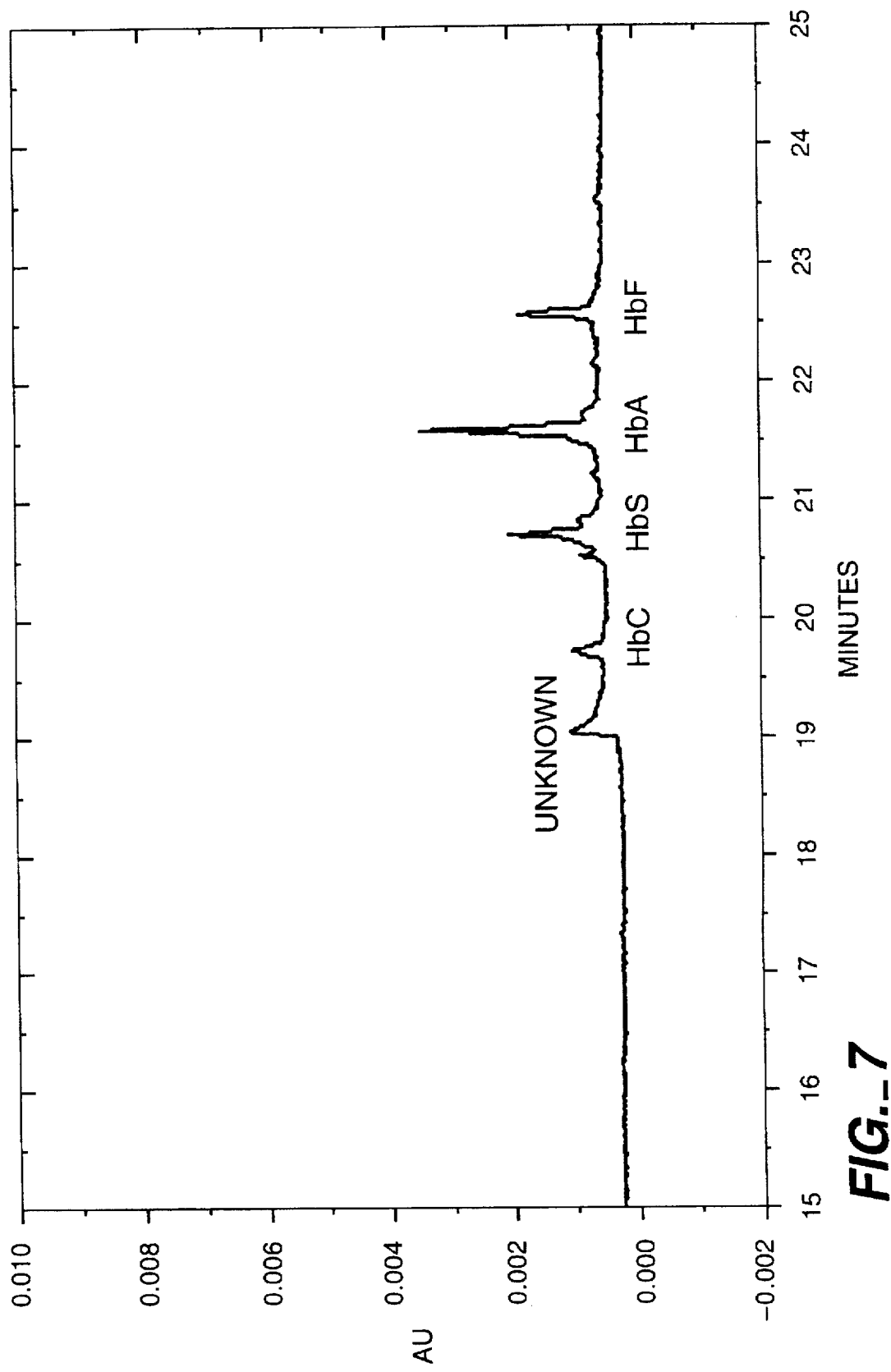
FIG._7

PREFORMED POLYMER COATING PROCESS AND PRODUCT

BACKGROUND OF THE INVENTION

Capillary Electrophoresis (CE) has emerged as an important tool for analyzing biomolecules. The high efficiency, high resolution, and automation capabilities of CE make it highly suitable in the routine analysis of proteins, peptides, and even small ions. A major problem encountered in the above separations is the interaction of basic analytes, such as basic proteins, with exposed surface silanol groups on the capillary wall. This interaction results in a loss of efficiency and irreproducible separations. Typical approaches in addressing the above problem include working at conditions where the silanol groups are either un-ionized[1] or fully ionized[2]. These conditions, however, entail working at extremes of pH and may be unsuitable for many analytes. Additionally, silica dissolves at extreme pH's, which is another limitation of this approach.[3] Other approaches in addressing the above problem involve adding compounds[4-6] that compete with the analytes for interaction sites on the capillary wall. These additives, however, may adversely affect the separation of analytes.

Another popular approach includes working with coatings that are either physically adsorbed or chemically attached to the capillary surface.[7-21] These coatings mask the presence of surface silanols and enhance separation efficiency. The adsorbed coatings suffer from limited stability and require repeated replenishment for effective operation[7]. Recently, Gilges et al.[7] showed excellent separation of basic proteins using a polyvinylalcohol (PVA) coated capillary. The polymer coating was achieved by a thermal treatment that immobilized PVA on the capillary wall. This coated capillary gave a low electroosmotic (EO) flow up to pH 9. However, only 40 runs were possible at pH 8.5 without loss of efficiency. Buffers such as borate, Tris HCl, and Triphosphate did not provide good separation of proteins using this coated capillary, thus limiting its utility.

A review of coatings for CE reveals several examples of chemically modified capillaries that were designed to minimize the presence of surface silanols and reduce analyte interactions. These modifications involve attaching or creating one or more polymeric layers on the surface of the capillary through various coupling chemistries. In 1985, Hjerten[8] showed a two-step coating process by attaching a bifunctional silane on the surface of the capillary followed by in situ polymerization of a vinyl group containing monomer. The presence of a polymerizable C=C group was essential in both the monomer and silane for coupling. Strege and Lagu[9] showed that the above coating gives a very low EO flow, but achieved poor separations of a mixture of proteins. The poor peak shapes obtained with this capillary were attributed to electrostatic and/or hydrogen bonding interactions of the proteins with the capillary wall or coating. It was necessary to incorporate a surfactant in the CE run buffer to achieve good separations of proteins. Similarly, a cross-linked in situ polymerized polyacrylamide capillary gave poor separation efficiencies for basic proteins when tested with no added cationic additives in the buffer[10].

As an alternative approach to in situ polymerization, coatings are formed by reacting silanes that have appropriate reactive end groups with reactive end groups on prederivatized polymers. These coatings were disclosed by Herren et al.[11] to mininize or reduce EO flow. They discussed several synthetic procedures for creating various derivatives of dextran[12] and PEG[13] and their utility in several applications including modifying control pore glass beads. However, data on the pH stability of this coating and its performance with proteins as test analytes were not shown. Following a similar approach, Hjerten and Kubo[14] showed the attachment of several polymers (e.g., methylcellulose and dextran) after a prederivatization step. The prederivatization step was required prior to attaching the polymers to the methacryl silane treated capillary. Additionally, the polymer coupling process was dependent upon a high yield of the prederivatization reaction.

Recently, Malik et al.[15,16] adapted a GC-type static coating procedure, in which the coating was achieved by depositing a mixture of polymer, initiators, and silane reagent on the surface of a capillary by using a low boiling point solvent. The capillary was then heat treated to cross-link the surface film. The coating thickness influenced the EO flow and performance and required optimization. In comparing data from Malik et al.,[15,16] variabilities in efficiencies were observed between analytes in a Superox-4 coated capillary and between two Superox-4 coated capillaries. Similarly, two Ucon 75-H-90000 polymer coated capillaries tested under identical conditions gave different migration times and mobilities, indicating problems with the reproducibility of the coating process.

The above coatings were attached through Si—O—Si—C linkage. To overcome the limited pH stability of the Si—O—Si bond, several researchers used approaches such as attaching polyacrylamide by in situ polymerization through a Si—C linkage[17] and attaching a hydrolytically stable derivative of acrylamide by in situ polymerization.[18] These approaches enhanced the coating stability relative to Hjerten's original approach and provided better efficiencies for basic proteins. However, multiple reaction steps with stringent conditions were required during the coating process. For example, the approach by Cobb et al.[17] required anhydrous solvents and conditions during the Grignard reaction step. Similarly, the work by Chiari et al.[18] required synthesis of a special monomer to achieve a stable and efficient coating. Other approaches involved cross-linking or attaching several polymeric layers on the capillary surface. Increased coverage on the capillary surface by the various polymeric layers was expected to diminish any interaction of the analytes with the exposed surface silanols. Smith et al.[19] showed separations of proteins in coated capillaries that had a primary silane layer anchored to several polymeric layers. Some layers were adsorbed on top of the primary layer. Huang et al.[20] showed separation of proteins using a cross-linked, immobilized, hydrophilic polymer layer atop a hydrophobic, self assembled, alkyl silane layer. Schmalzing et al.[21] showed excellent separations of basic proteins in a multilayered cross-linked coated capillary. In situ polymerization of a monomer on top of a cross-linked primary silane layer resulted in a hydrophilic polymeric layer that was subsequently cross-linked. The above approaches were all multistep processes and, in some cases, required additional cross-linking steps.[21]

There is a need for a simple method for coupling preformed underivatized polymers covalently to the surface of a conduit such as a fused silica capillary used for capillary electrophoresis.

In addition, polymer based support surfaces have been used for separating the components in a fluid stream such as for capillary electrophoresis or liquid chromatography. Such polymeric support surfaces can be on the inner walls of the conduit (e.g. capillary), or can form a packing of polymeric particles for liquid chromatography. In some instances, such polymeric support surfaces do not have the desired properties for separating components. For this purpose, such surfaces have been modified by coating with suitable hydrophilic polymers as disclosed in Afeyan et al. (U.S. Pat. No. 5,503,933).

SUMMARY OF THE INVENTION

An object of the invention is to provide a cross-linked coating of preformed polymer directly or indirectly covalently linked to the surface of the support. In one embodiment, an intermediate coupling agent is used between the support surface and the preformed polymer while, in the other embodiment, it is not.

Referring first to the coupling agent embodiment, a solid support according to the present invention has a coating on its surface which alters the properties of the support surface for separating components in a fluid stream in contact therewith. The coating comprises a coupling agent including a functional group and is covalently bound to said support surface in a substantially uniform layer, and a preformed polymer comprising totally saturated, substituted or unsubstituted, carbon chain backbones from which leaving groups have been abstracted while in solution and in contact with said coupling agent layer to form bonding sites on said preformed polymer which covalently bind to said coupling agent and which crosslink said preformed polymer forming a coating comprising a three-dimensional, cross-linked polymer network on said solid support.

The invention also includes a method of coating the solid support surface which alters the properties of the support surface for separating components in a fluid stream. The method comprises (a) covalently binding a coupling agent (including functional groups capable of forming free radical sites under hydrogen abstraction conditions) to said support surface in a uniform layer, and (b) thereafter, contacting said covalently bound coupling agent with a solution of said preformed polymer comprising totally saturated, substituted or unsubstituted, carbon chain backbones including leaving groups, under hydrogen abstraction conditions of elevated temperature in the presence of a free radical catalyst, said support surface not being soluble in said polymer, to remove leaving groups from said preformed polymer carbon chains to form free radical carbon binding sites which covalently bond to said coupling agent layer and to crosslink at least some of said preformed polymer through thus-formed free radical carbon binding sites therein to form a dimensional polymer network coating on said solid support surface.

In one instance, the second functional group in the coupling agent is typically a carbon moiety bound to a leaving group such as a reactive group (e.g. a halogen) or hydrogen. The leaving group is capable of being abstracted to a free radical under hydrogen abstraction conditions. For a coupling agent including carbon chain, the reactive groups or hydrogen may be terminal groups or interior of the carbon chain. In another embodiment a coupling agent including a carbon chain includes a second functional group in the form of unsaturation in the carbon chain (e.g. a terminal double bond) (C=C). Such unsaturated groups react with the free radical sites on the preformed polymer by a free radical addition reaction.

In the above method and coated solid support, one preferred support surface comprises silica with a coupling agent comprising a silane. Preferred leaving groups are hydrogen or halogens. The solid support preferably is either the inner wall of a capillary for capillary electrophoresis or the packing of a flow-through particle bed such as one used for liquid chromatography.

In another embodiment of the invention, no intermediate coupling agent is used for coating an organic polymeric solid support which has saturated or unsaturated carbon chains including functional groups capable of forming free radical sites under hydrogen abstraction conditions to alter the properties of separating components in a fluid stream in contact therewith. The coating comprises preformed polymer including totally saturated substituted or unsubstituted carbon chain backbones from which leaving groups have been abstracted while in solution and in contact with said support surface to form free radical binding sites on said preformed polymer and covalently bound to free radical binding sites formed on said support surface functional groups, and to crosslink said preformed polymer forming a coating comprising a three-dimensional, cross-linked polymer network on said solid support.

One preferred method for coating the polymeric solid support surface comprises contacting said support surface with preformed polymer comprising totally saturated carbon chain backbones including leaving groups under hydrogen abstraction conditions of elevated temperature in the presence of a free radical catalyst, to abstract hydrogen or other leaving groups from said preformed polymer carbon chains to form abstracted carbon sites which covalently bond said support surface to carbon chains, and to crosslink at least some of said preformed polymer through free radicals created at said hydrogen extraction carbon sites therein to form a three-dimensional polymer network coating on said solid support surface.

BRIEF DESCRIPTION OF THE DRAWINGS

FIG. 1 are electropherograms showing separations of basic proteins using various polymer coated capillaries.

FIG. 2 is a reproducibility study using a MET-PVP (360K) coated capillary.

FIG. 3 is a series of graphs slowing the effect of polymer molecular weight and concentration on efficiency of basic proteins.

FIG. 4 is a electropherogram illustrating acidic protein separations using a cationic polymer coated capillary.

FIG. 5 is a electropherogram illustrating separation of test anions using a cationic polymer coated capillary.

FIG. 6 is a electropherogram illustrating separation of proteins from 2% Vitamin D Milk using a MET-PVP coated capillary.

FIG. 7 is a electropherogram illustrating separation of hemoglobin variants using a MET-PVP coated capillary.

DETAILED DESCRIPTION OF THE PREFERRED EMBODIMENTS

The invention is directed to modifying the properties of a solid support surface for separating components in a fluid stream in contact with such surface. In one embodiment, the support surface comprises the inner wall of a conduit such as a capillary for capillary electrophoresis or capillary electrochromatography or capillary liquid chromatography or supercritical fluid chromatography or gas chromatography. In another embodiment, the solid support surface comprises the particulate packing of a flow-through particle bed used for liquid chromatography or capillary electrochromatography or supercritical fluid chromatography or gas chromatography. Other type of solid support surfaces useful in electrophoresis which could be modified according to the invention include silica or glass based microfabricated capillary array systems and slab-gel systems.

The invention will first be described with respect to the embodiment in which a coupling agent is used and in which the solid support surface is the inner wall of a capillary for capillary electrophoresis. However, it should be understood that the coupling agent mode could be used for other solid surfaces as described above.

A wide variety of solid support surfaces can be used so long as they are capable of covalent binding to a coupling agent which in turn is capable of covalent binding to a preformed polymer under hydrogen abstraction conditions. A common material used for the capillary in capillary electrophoresis is fused silica. Like other suitable support surfaces, it contains hydroxyl groups which are readily coupled to preferred coupling agents such as silanes. Suitable inorganic solid support surfaces containing hydroxyl groups, or groups convertible to hydroxyl groups, include silica, titania, quartz, glass, alumina, thoria, beryllia and zirconia.

Suitable coupling agents are ones which are capable of covalent binding to such support surfaces and, in turn, of covalent binding to the preformed polymer under hydrogen abstraction conditions as described below. Mechanisms of attachment of coupling agents to common support surfaces such as silica are well known such as illustrated in Hjerten U.S. Pat. No. 4,680,201. These coupling agents typically are bifunctional compounds with a first functional group capable of covalent attachment to the solid support surface and a second functional group (in the form of a leaving group) capable of binding to the preformed polymer. Suitable coupling agent first functional groups capable of binding the solid support include mono, di and tri alkoxy groups such as methoxy and ethoxy groups and halogens such as chlorine. As described, after one of the functional groups of the coupling agents is bound to the support surface, the coupling agent still includes a second functional group capable of forming a free radical binding site which covalently binds the preformed polymer. Such second functional group could be a saturated carbon chain in which the bound hydrogen is a leaving group. Alternatively, the second functional group could be a leaving group such as hydrogen or a halogen. Moreover, the second functional group could be unsaturation, e.g. in the form of C=C bonds capable of forming free radicals under hydrogen abstraction conditions. For purposes of the present invention, all of such coupling agent groups capable of binding the preformed polymer under hydrogen abstraction conditions are termed "second functional groups".

In the present process, the free radical binding sites are formed at the coupling agent second functional groups under hydrogen abstraction conditions by the removal of a leaving group or breaking of a C=C double bond. At the same time, the preformed polymer in solution also forms a free radical binding site in contact with the coupling agent free radical binding site to form a covalent bonding between the coupling agent layer and the preformed polymer.

The principles that govern the lability or ease of release of leaving groups are well known. Encyclopedia of Polymer Science and Engineering, Vol. 13, p.818, Lenz, R. W. Organic Chemistry of Synthetic High Polymers, (1967) pp. 288–289, and Encyclopedia of Polymer Science & Engineering, Vol. 13, p.714. For example, release of steric compression on radical formation partially accounts for the progressive decrease in the strength of C—H bonds from primary to secondary to tertiary. Important labile hydrogen groups include protons on the carbonyl functions of aldehydes and formate esters, on the carbinol functions of primary or secondary alcohols, on the α-carbon atoms of amines and ethers, on the thiol functions of mercaptans and on carbon atoms adjacent to unsaturated functions. Abstraction of leaving group abstraction follows the order of strength of the bonds being broken, except for abstraction of hydrogen:

Chlorine, bromine and iodine are very labile (e.g. in polyhalomethanes and other haloalkanes).

One preferred form of coupling agent is a silane. Suitable silanes in general can be designated as $R_{(n)}SiX_{(4-n)}$. Here, the X group reacts with the substrate and this results in a covalent bond between the substrate and the silane. X is a hydrolyzable group and includes mono, di or tri substituted alkoxy such as methoxy or ethoxy, or halogen groups such as chlorine. The R group consists of a non-hydrolyzable organic chain which includes end-group fluctionalities such as acetoxy or acryloxy or allyl or amino or alkyl or benzyl, or vinyl groups. R may also includes other suitable functionalities such as halo or cyano or thiocyano or mercapto groups. Suitable silanes are listed in 1) Silicon Compounds: Register & Review, from United Chemical Technologies, 5th Ed., 1991, and in (2) Tailoring Surfaces with Silanes, Chemtech 7, 766 (1977). They include allyltrimethoxysilane, chlorodimethyloctylsilane, γ-methacryloxypropyltrimethoxysilane, 3-aminopropyltrimethoxysilane and 3-glycidoxypropyltrimethoxysilane.

The coating process described herein requires no reactive functionalities for coupling, either on the polymer or on the silane. Free radical sites formed on both the polymer and the silane are sufficient for simultaneous coupling and cross-linking. No special conditions are required for this coupling reaction. The capillaries coated by the above process satisfy the four major requirements of a coated capillary for CE; namely: (1) provide reproducible separation of analytes through generation of reproducible EO flow; (2) allow minimal interaction with the analytes, thus maximizing efficiency of the separation and recovery, (3) show minimal absorbance at the monitored wavelength for enhanced sensitivity, and (4) retain stable performance under a variety of buffer and pH conditions for robust operation.

As is well recognized, a silane coupling agent bound to a silica solid support surface forms Si—O—Si linkages. Silicon Compounds: Registry & Review from United Technologies, 5th Ed. p.59. However, coupling agents other than silanes may be employed to provide different coupling linkages. For example, an allyl methacrylate coupling agent may be bound to a silica surface by Si—C linkage[17]. Other coupling agents with silica walls include an alcohol (after treatment with thionyl chloride reagent) which form a Si—O—C linkage (Snyder, L. R. & Kirkland, J. J., Introduction to Modern Liquid Chromatography, John Wiley & Sons, Inc., 1979, Chapter 7, p.272–3). Yet, another coupling agent of the amine type produces Si—N linkage (after treatment with thionyl chloride reagent). Snyder, Supra. Analogous linkages are formed between silanes and hydroxyl-containing solid support surfaces other than silica (e.g. Ti—O—Si) (Matyska et al., in Poster #P-0561, 20th International Symposium of High Performance Liquid Phase Separations and Related Techniques, June 1996, San Francisco, Calif.).

The preformed polymer of the present invention is coupled to the free radical sites formed at least in part by removal of leaving groups in the preformed polymer backbone under hydrogen abstraction conditions. The same principles apply to selection of suitable leaving groups for the coupling agent as for the preformed polymer. The preformed polymer is formed of totally saturated carbon chain backbones which have not been prederivatized to form unsaturation prior to covalent bonding with a coupling agent. However, the preformed polymer may include unsaturation in carbon side chains or moieties, such as aromatic groups, including benzene rings, e.g. in polystyrene. The carbon chain backbones typically include from 50 to 10,000 carbons in the chains. They may be of any suitable length to provide the desired property so long as they include leaving groups which are abstracted under hydrogen abstraction conditions to form covalent bonds with the coupling agent which has previously been covalently bound to the support surface.

For a smooth or regular surface such as the inner wall of a capillary, the coupling agent binds in a substantially uniform layer to the support surface. That is, it substantially covers the support surface by interacting with the available reactive sites on such surface when it is uniformly available as the inner wall of a capillary. If the surface is irregular such as the pores of a macroporous surface, there would be corresponding irregularity in the uniformity of the coating.

The carbon chains, typically polymerized, of the preformed polymer may be unsubstituted, i.e. include only hydrogen groups along the chain which are abstractable under hydrogen abstraction condition to form free radical sites. Alternatively, the carbon chains may be substituted by a variety of groups or moieties which can serve different purposes. For example, the group may comprise leaving groups (e.g. halogen) which are abstracted to form the free radical bonding sites for bonding to the coupling agent and for cross-linking. Other substituted leaving groups include hydrogen bound to sulfur as in mercapto "SH" groups typically at the end of the chain. Also, the substitution may comprise non-leaving groups which serves the function of altering the properties of the support surface for separating the components in the fluid stream. For example, a quaternary nitrogen atom imparts ion exchange selectivity to the support surface after it is bound. Similarly, an OH group imparts hydrophilicity to the support surface after it is bound.

A suitable list of preformed polymers which include appropriate leaving groups and also the ability to alter characteristics include substituted or unsubstituted polyalkylenes, polyesters, polyamines, polyamindes, polyethers, polysufonates, polyoxides, polyalkyleneglycols, polystyrenic based polymers, polyacetals, polychlorides, polysaccharides, polycarbonates, polymers of monoethylenically unsaturated monomers, polymers of polyvinylidene monomers and mixtures and copolymers of the above polymers. Preferred suitable specific preformed polymers include polyethyleneoxide, polyacrylamide, polyvinylalcohol, polyvinylpyrolidone, polyethyleneglycol, acrylamidomethylpropylsulfonic acid, polyacrylic acid and methacrylamidopropyltrimethylammonium chloride.

Other characteristics of the preformed organic polymer are that they be sufficiently soluble in solvent to uniformly coat the solid support surface without dissolving the solid support. Suitable solvents include water, alcohols such as methanol, ethanol, polyols such as glycerine, ethylene glycol, ketone-alcohols such as diacetone alcohol, acids such as formic acid, acetic acid, ether-alcohols such as glycol ethers, lactones such as γ-butryolactone, esters such as ethyl lactate, ethyl acetate, ketones such as methylcyclohexanone, acetone, chlorinated hydrocarbons such as methylene dichloride, chloroform, carbon tetrachloride, lactams such as 2-pyrolidone, N-methyl-2-pyrolidone, amines such as butylamine, cyclohexylamine, aniline, morpholine, nitroparaffins such as nitromethanes, hydrocarbons such as benzene, toluene, hexane, alone or in combination with other solvents, ethers such as dioxane, tetrahydrofuran, chlorofluoroalkanes such as dichloromonofluoromethane, inorganic solutions of salts such as aluminium potassium sulfate, ammonium chloride, ferric chloride, sodium chloride, potassium chloride, etc.

The separation characteristic of the coating can be used in a wide variety of applications. For example, it could be used in capillary electrophoresis in which the coating can vary EO flow. The coating can be anionic, cationic or neutral, depending on the desired effect. The coating substantially covers the solid surface. It covalently bonds in a cross-linked three-dimensional matrix between preformed polymer chains and with the coupling agent. This cross-linked coating is highly stable. It is stable over a wide pH range (e.g. 2 to 10) due to its high level of cross-linking on the surface. The extent of substitution on the polymer chain and on the coupling agent (e.g. silane) together with type of solvent and initiator system,[22] determines the extent of cross-linking and coupling.

Referring back to the method of formation, the coupling agent is first covalently bonded to the support surface as described above. Thereafter, the preformed polymer is dissolved in a suitable solvent in which it is soluble. However, the solid support surface remains in a solid form, i.e. it maintains the integrity of its shape, (e.g. at the inner wall of the capillary or particles). The relative solubility characteristics of the support surfaces and preformed polymers are well known.

Suitable free radical catalysts include ammonium persulfate, hydrogen peroxide, hydrazine and a20 based catalysts. Cross-linking of neutral polymer coatings are formed by cross-linking polymers such as PVP,[23,24] polystyrene or polyvinyl acetate[25] by treating with the above free radical catalyst at elevated temperature. The general mechanism of cross-linking with these free radical catalysts includes abstracting hydrogen atoms from the polymer chain by $SO_4^-$ or $OH^-$ radicals.[26]

The molecular weight of the preformed polymer may be varied over a wide range so long as it is capable of being dissolved for uniform contact with the support surface. Typical molecular weights may vary from 5,000 to as high as 1,000,000 or more.

One of the features of the present invention is that under hydrogen abstraction conditions, the preformed polymer covalently links to the coupling agent and simultaneously cross-links to form a coating comprising a three-dimensional polymer network on the support structure. This cross-linked nature provides high pH stability to the surface coating and inhibits nonspecific interactions of the analyte with the surface. Cross-linking occurs in the coating and can be verified from literature on cross-linking of polymers. Experimental verification of cross-linking was done by solution phase experiments where the linear polymer dissolves in normally used solvents whereas the cross-linked polymers does not. High pH stability of this coating compared to linear polymer coating is an indirect verification of cross-linking.

The hydrogen abstraction conditions according to the present invention are the conditions well known for hydrogen abstraction from polymers. Encyclopedia of Polymer Science and Engineering, John Wiley & Sons, New York, (1990) Vol. 4, p.385;[24,25]. The conditions include elevated temperatures for a sufficient holding time in the presence of a free radical catalyst. By "elevated temperatures" means a temperature in excess of room temperature, typically from a minimum of 40° C. to as high as 150° C. The temperature may vary with the labile characteristics of the leaving group in the covalently bound coupling agent and in the preformed polymer, the type of free radical catalyst, and the like. The solvent used will either enhance the formation of cross-linking by transferring the low molecular weight radical to the polymer chain or the solvent radical will minimize the formation of cross-links by combining with macro radicals.

In a preferred embodiment fully formed polymers are coated onto the surface of a fused silica capillary. No additional derivatization of the polymer is required prior to coupling. The coating is achieved by polymer macroradicals formed during the cross-linking process. The polymer becomes attached to the surface of a silane treated capillary through the same radical mechanism. Cross-linking between the polymer chains and coupling to the silane takes place simultaneously. At a minimum, cross-linking occurs through bonding sites created on the preformed polymer carbon backbones. However, additional cross-linking may take place through bonding sites pre-treated on the preformed polymer side chains. The resulting coating is a highly cross-linked, stable layer on the capillary surface. The pH stability of this coating is improved over existing coatings, due to the high level of cross-linking on the capillary surface. No specific leaving groups other than hydrogen are necessary on the silane or on the polymer for the coupling process to take place. However, the extent of substitution on the polymer chain and the silane, coupled with the solvent and the initiator system,[22] determines the extent of cross-linking and coupling.

According to the invention, cross-linking of polymers, such as PVP,[23, 24] polystyrene and polyvinylacetate[25] can be achieved by treating the polymer with free radical initiators such as ammonium persulfate, hydrogen peroxide, and hydrazine. The general mechanism of cross-linking involves abstracting hydrogen atoms from the polymer chain by $SO_4^-$ or OH radicals.[26] The macroradicals formed then combine to form cross-links. Competing reactions include dissociation of the polymer chain, in some cases generating some few radical- and vinyl-terminated polymer chains. The solvent used will either enhance the formation of cross-links by transferring the low molecular weight radical to the polymer chain, or the solvent radical will minimize the formation of cross-links by combining with macroradicals.

ORGANIC POLYMERIC SOLID SUPPORT EMBODIMENT

In the use of a suitable organic polymeric solid support, the coating of the present invention may be formed without a coupling agent. The polymeric solid support of the present invention has saturated or unsaturated carbon chains including leaving groups in the polymer backbone or in side chains, including cross-links. The above discussion of "carbon chains", "saturated" or "unsaturated" and "leaving groups" for the preformed polymer apply to the organic polymeric solid support. In this instance, the polymeric support material has the requisite functional groups for covalently bonding directly to the preformed polymer under hydrogen abstraction conditions without the requirement for a separate coupling agent. In that regard, the carbon chains with the functional groups may be present after polymerization of one or more monomers to form a homopolymer or copolymer. For example, a suitable copolymer would be the well known copolymer styrene-divinyl benzene used as the resin particles in a packed bed for liquid chromatography. In this instance, the polymer includes the residual unsaturated linkages from divinyl benzene.

Suitable monopolymers include homopolymers of polyvinylidene monomer. Suitable copolymers include copolymer of polyvinylidene monomer and monovinylidene monomer.

In addition to copolymers, suitable polymeric support particles include polymers with grafted side chains or block copolymers or any other derivatized polymer so long as the polymeric support includes the requisite functional groups at the time of reaction with the preformed polymer. Suitable substrates of this type include substrates containing surface hydroxyl groups, for example, copolymers of divinylbenzene, styrene and vinylbenzylchloride, which are base esterified for reacting with preformed polymer. In that regard, in the broad sense a coupling agent may be used to provide possible reactive sites on the organic polymeric support prior to covalent bonding with the preformed polymer. Suitable bifunctional coupling agents which bind the organic polymeric support particles to the preformed polymer include acrylic anhydrides, acryloyl chlorides, vinyl benzyl chlorides and the like. Reactants of this type are known to those skilled in the art and are listed in general organic chemistry books such as Advanced Organic Chemistry, Reaction, Mechanism & Structure by Jerry March (John Wiley & Sons, Inc. 1992).

The same hydrogen abstraction conditions discussed above regarding the coupling agent bound inorganic solid supports generally apply to this organic polymer solid support. Also, the same types of preformed polymers described above may be used as the preformed polymers in this embodiment.

The polymer is attached through multiple linkages on the surface of the substrate, thus enhancing the pH stability of the coating. In the above coupling process, stringent control of reaction conditions is not required since the polymer is already formed. In situ polymerized coatings on the other hand, require stringent control of such variables as oxygen levels and temperature[27] because the polymer has to be created on the surface.

In order to illustrate the present invention, the following examples are provided.

EXAMPLE 1

A 3-Methacryloxypropyltrimethoxysilane Coupled to Polyvinyl Pyrrolidone (PVP) Polymer Capillary preparation: The inner wall of the capillary (formed of silica) is first rinsed with 1M NaOH for at least 10 minutes with an applied pressure of 10 psi, followed by deionized water. The capillary is then rinsed with 1% (w/v) acetic acid in water for 2 hours.

Silanization: A 1% solution (v/v) of 3-methacryloxypropyltrimethoxysilane in 1% acetic acid is prepared and the capillary is rinsed with this solution for 1 hour using 10 psi pressure. The capillary is stored in the silane solution for at least 24 hours and then displaced with deionized water.

Polymer solution preparation: A 4% PVP (MW: 360,000) solution in water is prepared. 5 µl of TEMED and 50 µl of a 10% ammonium persulfate (w/w) is added to 10 ml of the above polymer solution. The above solution is then pressurized into the silanized capillary by applying 10 psi pressure.

Polymer bonding step: The capillary filled with the polymer solution is placed in an oven with the ends sealed, and baked at 80° C. for 18 hours. The capillary is rinsed with deionized water and is ready for testing.

EXAMPLE 2

An Allyl Silane is Coupled to Polyvinyl Pyrrolidone (PVP) Preformed Polymer

All the steps are identical to Example 1 except the silane was an allyltrimethoxysilane.

EXAMPLE 3

Chlorodimethyloctyl Silane is Coupled to a PVP Polymer

All the steps are identical to Example 1 except the silane is prepared as a 2% solution in ethanol.

EXAMPLE 4

A 3-Methacryloxypropyltrimethoxysilane is Coupled to Polyacrylamide Preformed Polymer All the steps are identical to Example 1 except the preferred polymer is polyacrylamide and is prepared as a 2% solution in water.

EXAMPLE 5

A 3-Methacryloxypropyltrimethoxysilane Coupled to an Anionic Polyacrylamide Polymer Conditions similar to example 4 except the preferred polymer is 2% anionic polyacrylamide.

EXAMPLE 6

A 3-Methacryloxypropyltrimethoxysilane is Coupled to a Preformed Cationic Polymer All conditions are the same as Example 1 except the polymer is a copolymer of 2% (w/w) acrylamide and 1.8% (w/w) methacrylamidopropyltrimethylammonium chloride.

EXAMPLE 7

A 3-Methacryloxypropyltrimethoxysilane Coupled to PVP Polymer Using a Different Free Radical Initiator All the conditions are the same as example 1 except 4,4'-Azo-bis-(4-cyano pentanoic acid) was used instead of ammonium persulfate and TEMED. 61.5 µl of a 10% solution (w/w) of 4,4'- Azo-bis-(4-cyano pentanoic acid) in methanol was added to 10 ml of a 4% PVP polymer solution.

EXAMPLE 8

Anionic Polymer Attached to Silica Particles Suitable for Use as a Packing

A. Silica pretreatment 15 µm silica particles with 150 Å pore size (grade 215hp4X 1930) was obtained from Davisil. 30.15 g of deionized water was added to 4.77 g of the above silica material and dispersed uniformly. 2.23 g of Conc. Nitric acid was added and the mixture was heated in an oven for 18 hours at 52° C. The material was removed after the heat treatment and washed with deionized water until the pH of the water was measured to be neutral. After removal of water the material redispersed in deionized water to a total weight of 54.14 g followed by addition of 0.65 g of acetic acid and 0.5 g of methacryloxypropyltrimethoxy silane reagent. The material was dispersed uniformly and heated in an oven for 18 hours at 52° C.

B. Preforming polymers: 0.98 g of 2-acrylamido-2-methyl propane sulfonic acid (AMPS) (Monomer Polymer & DAJAC Laboratories, Pa., USA) and 0.98 g of acrylamide (BDH Laboratories, Poole, England) was dissolved in 16.6 g of deionized water and degassed. 0.024 g of VA 086 Azo initiator (Wako Pure Chemical Industries Ltd., Japan) was added to the above monomer mixture and the mixture was placed in an oven at 52° C. for 18 hours. The resulting polymer was a copolymer of AMPS and acrylamide. The above polymer was weighed, followed by precipitation with suitable solvent. The precipitated polymer was then redissolved and reconstituted to the original weight in deionized water.

C. Attachment to silica particle: 18 g of the pretreated silica slurry from step A was washed with deionized water, acetone and followed by deionized water. The final weight of the silica material was adjusted to 10 g with deionized water 1 g of the polymer from step B was added to the above and 0.02 g of VA 086 Azo initiator (Wako Pure Chemical Industries Ltd., Japan) was added. The entire material was dispersed homogeneously and then placed in an oven at 80° C. for 18 hours. The resulting covalently bonded material from above was washed with water followed by 100 mM acetic acid before packing in an analytical column using standard methods and apparatus at 6000 psi for 10 minutes. This silica bonded polymer column is suitable for chromatographic separations of inorganic cations and other macromolecules. The above silica bonded polymeric material when packed in capillaries is suitable for electrochromatographic separations of inorganic cations and other macromolecules.

EXAMPLE 9

Anionic Polymer is Attached to Polymeric Particles Suitable for Use as a Packing A. 2.4 g of a dried 55% cross-linked macroporous resin (substrate is ethylvinylbenzene cross-linked with 55% divinylbenzene, resin preparation described in U.S. Pat. No. 4,224,415) was dispersed in 4 g of tetrahydrofuran and 5 g of water was added to this slurry. 1 g of polymer solution prepared as shown in Example 9 step B was added to this slurry. 0.02 g of VA 086 Azo initiator (Wako Pure Chemical Industries Ltd., Japan) was added and the entire material was dispersed homogeneously and then placed in an oven at 80° C. for 18 hours. The resultant polymeric material from above was washed with water followed by 100 mM acetic acid before packing in an analytical column using standard methods and apparatus at 6000 psi for 10 minutes. This polymeric column is suitable for chromatographic separations of inorganic cations and other macromolecules. The above polymeric material when packed in capillaries is suitable for electrochromatographic separations of inorganic cations and other macromolecules.

EXAMPLE 10

Cationic Polymer Attached to Silica Particles Suitable for Use as a Packing

A. Preforming polymers: 0.98 g of methacrylamidopropyltrimethyl-ammonium chloride and 0.98 g of acrylamide (BDH Laboratories, Poole, England) was dissolved in 16.6 g of deionized water and degassed. 0.024 g of VA 086 Azo initiator (Wako Pure Chemical Industries Ltd., Japan) was added to the above monomer mixture and the mixture was placed in an oven at 52° C. for 18 hours. The resulting polymer was a copolymer of methacrylamidopropyltrimethyl-ammonium chloride and acrylamide. The above polymer was weighed, followed by precipitation with suitable solvent. The precipitated polymer was then redissolved and reconstituted to the original weight in deionized water.

Attachment to silica particle: 18 g of pretreated silica from step A in Example 8 was washed with deionized water, acetone and followed by deionized water. The final weight of the silica material was adjusted to 10 g with deionized water. 1 g of polymer solution from step A in Example 10 was added to the silica material in water followed by 0.02 g of VA 086 Azo initiator (Wako Pure Chemical Industries Ltd., Japan) The entire material was dispersed homogeneously and then placed in an oven at 80° C. for 18 hours. The resulting polymer bonded material from above was washed with water followed by 100 mM citrate buffer at pH 6.0 before packing in an analytical column using standard methods ant apparatus at 6000 psi for 10 minutes. This silica bonded polymer column is suitable for chromatographic separation of inorganic anions and other macromolecules. The above polymer bonded silica material when packed in capillaries is also suitable for electrochromatographic separation of inorganic anions and other macromolecules.

EXAMPLE 11

Cationic Polymer is Attached to Polymeric Particles Suitable for Use as a Packing A. 2.4 g of a dried 55% cross-linked macroporous resin (substrate is ethylvinylbenzene cross-linked with 55% divinylbenzene, resin preparation described in U.S. Pat. No. 4,224,415) was dispersed in 4 g of tetrahydrofuran and 5 g of water was added to this slurry. 1 g of polymer prepared as shown in Example 10 step A was added to this slurry. 0.02 g of VA 086 Azo initiator (Wako Pure Chemical Industries Ltd., Japan) was added and the entire material was dispersed homogeneously and then placed in an oven at 80° C. for 18 hours. The resultant polymeric material from above was washed with water and 100 mM sodium carbonate at pH 11 before packing in an analytical column using standard methods and apparatus at 6000 psi for 10 minutes. This column is a polymeric column suitable for chromatographic separation of inorganic anions and other macromolecules. The above polymeric material when packed in capillaries is also suitable for electrochromatographic separation of inorganic anions and other macromolecules.

EXAMPLE 12

Nonionic Polymer is Attached to Silica Particles Suitable for Use as a Packing

A. A 10% solution of polyvinylalcohol 25K (98% hydrolyzed from Polyscience Laboratories) was prepared in water.

B. 18 g of pretreated silica as shown in step A in Example 9 was prepared and washed with deionized water, acetone and followed by deionized water. The final weight of the silica material was adjusted to 10 g with deionized water. 1 g of polymer solution from step A was added to the silica material in water followed by 0.02 g of VA 086 Azo initiator (Wako Pure Chemical Industries Ltd., Japan). The entire material was dispersed homogeneously and then placed in an oven at 80° C. for 18 hours. The resulting polymer bonded material from above was washed with water followed by 100 mM acetic acid before packing in analytical column using standard methods and apparatus at 6000 psi for 10 minutes. This column is suitable for normal phase chromatographic separations and in size exclusion applications. The above polymer bonded silica material when packed in capillaries is suitable for electrochromatographic separations.

EXAMPLE 13

Nonionic Polymer Attached to Polymeric Particles Suitable for Use as a Packing

A. 2.4 g of a dried 55% cross-linked macroporous resin (substrate is ethylvinylbenzene cross-linked with 55% divinylbenzene, resin preparation (resin preparation described in U.S. Pat. No. 4,224,415) was dispersed in 4 g of tetrahydrofuran and 5 g of water was added to this slurry. 1 g of polymer prepared as shown in Example 12 step A was added to this slurry. 0.02 g of VA 086 Azo initiator (Wako Pure Chemical Industries Ltd, Japan) was added and the entire material was dispersed homogeneously and then placed in an oven at 80° C. for 18 hours. The resultant polymeric material from above was washed with water and 100 mM acetic acid before packing in an analytical column using standard methods and apparatus at 6000 psi for 10 minutes. This column is a polymeric column suitable for size exclusion separations. The above polymeric material is suitable for electrochromatographic separations.

EXAMPLE 14

Cationic Polymer is Attached to Polymer Particles Suitable for Use as a Packing

A. Preforming polymers: To 4.16 g of 2-methacryloxyethyltrimethylammonium chloride (70% in H20 from Polysciences Laboratories) was added 3.92 g of methanol and degassed prior to adding 0.03 g of VA 044 Azo initiator (Wako Pure Chemical Industries Ltd., Japan). The above mixture was placed in an oven for 18 hours at 52° C. to form a polymer of the above monomer.

B. Attachment to a polymeric particle: 0.4 g of polymer prepared as shown in step A was added to 5.1 g of water. The above mixture was initiated by adding 0.02 g of Azobiscyanovaleric acid initiator (Fluka Chemicals). 2.3 g of acetic acid is added to above mixture followed by 2.31 g of a dried 55% cross-linked macroporous resin (substrate is ethylvinylbenzene cross-linked with 55% divinylbenzene resin preparation described in U.S. Pat. No. 4,224,415) and dispersed. 4.7 g of ammonium hydroxide was added to above slurry and dispersed homogeneously and then placed in an oven at 52° C. for 8 hours. The resultant polymeric material from above was washed with 50 ml of deionized water, followed by 200 ml of acetone and followed by 50 ml of a 1×carbonate/bicarbonate solution (1.8 mM of sodium carbonate +1.7 mM of sodium hydrogen carbonate) and dispersed in a 10×carbonate/bicarbonate solution (18 mM sodium carbonate/17 mM sodium hydrogen carbonate) before packing in an analytical column using standard methods and apparatus at 6000 psi for 10 minutes. This column is a polymeric column suitable for chromatographic separation of inorganic anions and other macromolecules. The above polymeric material when packed in capillaries is also suitable for electrochromatographic separation of inorganic anions and other macromolecules.

EXAMPLE 15

Cationic Copolymer is Attached to Polymeric Particles Suitable for a Use as a Packing A. Preforming polymers: To 2.12 g of 2-methacryloxyethyltrimethylammonium chloride (70% in H20 from Polysciences Laboratories) was added 1.7 g of Vinylbenzylchloride (Dow Chemicals) and 5.67 g of methanol was added to this mixture and the solution was mixed and degassed prior to adding 0.02 g of VA 044 Azo initiator (Wako Pure Chemical Industries Ltd., Japan). The above mixture was placed in an oven for 18 hours at 52° C. to form a copolymer of the above monomers.

B. Attachment to a polymeric particle: 0.45 g of polymer prepared as shown in step A was added to 5.3 g of water. The above mixture was initiated by adding 0.02 g of Azobiscyanovaleric acid initiator (Fluka Chemicals). 2.37 g of acetic acid is added to above mixture followed by 23 g of a dried 55% cross-linked macroporous resin (resin preparation described in U.S. Pat. No. 4,224,415) and dispersed. 4.9 g of ammonium hydroxide was added to above slurry and dispersed homogeneously and then placed in an oven at 52° C. for 8 hours. The resultant polymeric material from above was washed with 50 ml of deionized water, followed by 200 ml of acetone and followed by 50 ml of a 1×carbonate/bicarbonate solution (1.8 mM of sodium carbonate +1.7 mM of sodium hydrogen carbonate) and dispersed in a 10×carbonate/bicarbonate solution (18 mM sodium carbonate/ 17 mM sodium hydrogen carbonate) before packing in an analytical column using standard methods and apparatus at 6000 psi for 10 minutes. This column is a polymeric column suitable for chromatographic separation of inorganic anions and other macromolecules. The above polymeric material when packed in capillaries is also suitable for electrochromatographic separation of inorganic anions and other macromolecules.

EXAMPLE 16

The separation of basic proteins in several polymer coated capillaries using the above bonding approach and a 50 mM sodium acetate buffer (pH 4.5) is shown in FIG. 1. FIG. 1 shows separations of basic proteins using various polymer coated capillaries. Capillary: 50 cm total length; 45 cm to detector; 50 µm i.d. Buffer: 50 mM sodium acetate at pH 4.5. Conditions: 20 kV (400 V/cm); Gravity Injection: 50 mm×10 s. Detection: V, 210 nm. Sample concentration: 100 µg/ml. Peak identification: (1) Lysozyme (Chicken Egg White), (2) Cytochrome c (Bovine Heart), (3) Ribonuclease A (Bovine Pancreas), (4) Myoglobin (Horse Skeletal Muscle), (5) a-Chymotrypsinogen A (Bovine Pancreas).

The basic proteins show approximately the same migration times in all the capillaries. The capillary-to-capillary migration time variation was 3.12% (RSD), indicating a small EO flow variation between the capillaries. The efficiency generated in capillaries treated with (a) 4% PVP on MET silane, (b) 4% PVP on octyl silane, and (c) 2% polyacrylamide on MET silane were similar (app. 500,000 plates/50 cm). We observed no band broadening effects or efficiency loss due to hydrogen bonding interactions with the polymer for the above polymer coatings, contrary to the observations of Zhao et al.[6] and Strege and Lagu[9]. Much lower efficiencies were generated in a PVP-coated-on-allyl silane capillary (160,000 plates/50 cm) and PEO on a MET silane (300,000 plates/50 cm). Hydrophobicity of the silane is probably not contributing to the loss of efficiency in the PVP-allyl silane coated capillary, because higher efficiencies were realized with an even more hydrophobic octyl silane on the PVP-octyl silane coated capillary. Although all the above coated capillaries produced a low EO flow, not all the silanols were modified by the coating process. Hence, performance of the coating was probably related to the extent of shielding of analytes from residual silanols. The extent of modification of the surface silanols by the primary silane layer, coupled with the level of coverage by the polymeric layer attached to the primary silane layer, determines the extent of shielding. These results suggest that both the silane and the polymer influenced the coating performance.

EXAMPLE 17

The stability of a MET-PVP coating was tested by running 500 repetitive analyses of a basic protein test mixture. The RSD of migration times was within 2% (n=500). The corrected migration times with respect to lysozyme (plotted in FIG. 2) showed an RSD of 0.42% (n=500). FIG. 2 is a reproducibility study using a MET-PVP (360K) coated capillary. All other conditions are the same as in FIG. 1.

EXAMPLE 18

The coating was further tested for interaction with basic proteins under a variety of concentration conditions. The response versus concentration plots showed good linearity, and correlation coefficients ($r^2$) higher than 0.995 were obtained for all the tested proteins. The capillary generated more than 250,000 plates at a concentration of 300 µg/ml and more than 100,000 plates at a concentration of 1 mg/ml. The RSD in migration times in the tested range of 5 µg/ml to 1000 µg/ml was 1.6%, consistent with the long term performance of this capillary. The concentration detection limit for basic proteins under our experimental conditions was 5 µg/ml. Based on the linearity of response versus concentration curves, high efficiency under high concentration conditions, low detection limit, and minimal migration time variation under high analyte concentrations, we conclude that the analytes interacted minimally with the coating surface.

The MET-PVP capillary remained stable under a variety of buffer and pH conditions. The EO mobility in this coated capillary was less than $2 \times 10^{-5}$ cm$^2$/V.s at pH 10 using a 10 mM borate buffer and tested for more than 48 hours. A fused silica capillary tested under the same conditions gave an EO mobility of $62.5 \times 10^{-5}$ cm$^2$/V.s. The EO flow was substantially reduced by the polymer coating. The EO mobility in the polymer coated capillary increased from $1.5 \times 10^{-5}$ cm$^2$/V.s to $5 \times 10-5$ cm$^2$/V.s after 40 h using a 50 mM sodium carbonate buffer at pH 11. At extremes of pH, the silanols slowly become exposed due to some coating loss. This is not an unusual finding, given the lack of stability of the Si—O—Si linkage and the dissolution of silica at high pH. In performing the pH stability studies, we observed that electrophoretic runs were important to establish stability rather than mere contact with the run buffer. The octylsilane-PVP capillary also remained stable at pH 10, and gave an EO mobility of $<2.5 \times 10^{-5}$ cm$^2$/V.s. The high stability of our coating is due to the high level of cross-linking on the surface of the capillary.

EXAMPLE 19

The effect of polymer size and concentration on the coating performance was studied by coating several capillaries under the same conditions and testing them for basic protein separations using a 50 mM sodium acetate buffer at pH 4.5. (See Table 1 and FIG. 3). FIG. 3 shows the effect of polymer molecular weight and concentration on efficiency of basic proteins. All other conditions are the same as in FIG. 1.

TABLE I

Effect of Polymer Size and Concentration on Migration Time
Average Migration Time in Minutes (n = 3)

| Polymer size and Concentration | Lysozyme | Cytochrome c | Ribonuclease A | Myoglobin | α-Chymotrypsinogen |
|---|---|---|---|---|---|
| PVP 10K 4% | 9.11 | 9.49 | 12.37 | 12.92 | 15.08 |
| PVP 360K 4% | 9.35 | 9.81 | 12.87 | 13.3 | 15.60 |

TABLE I-continued

Effect of Polymer Size and Concentration on Migration Time
Average Migration Time in Minutes (n = 3)

| Polymer size and Concentration | Lyso-zyme | Cyto-chrome c | Ribo-nuclease A | Myo-globin | α-Chymotryp-sinogen |
|---|---|---|---|---|---|
| PVP 1M 4% | 9.39 | 9.86 | 12.81 | 13.34 | 15.65 |
| PVP 360K 1% | 9.15 | 9.6 | 12.45 | 13 | 15.20 |
| PVP 360K 10% | 9.33 | 9.78 | 12.72 | 13.26 | 15.56 |
| % RSD | 1.37 | 1.61 | 1.76 | 1.45 | 1.68 |

The average efficiency was almost the same based on an RSD of less than 5%. The RSD in migration times for the various proteins was less than 2%, indicating that polymer size and concentration had a minimal influence on the coating performance. These results also indicated that the EO flow and shielding of surface silanols were nearly identical in these capillaries. Testing under alkaline conditions using a phosphate buffer at pH 8 gave an average EO flow of $<1.7\times10^{-5}$ cm$^2$/V.s for all the capillaries (tested for more than 24 hours). The coating process was insensitive to the molecular weight change and concentration of the polymer. No optimization of the polymer size or concentration was required to achieve optimal performance, unlike the approach of Zhao et al.[16] Additionally, the coating thickness was optimal based on the high efficiencies observed using these coatings.

EXAMPLE 20

Replacing the persulfate initiator system with an azo-based initiator system resulted in minimal change in performance for the MET-PVP capillary. The average efficiency for basic proteins in a MET-PVP coated capillary using an azo initiator was ~500,000 plates/capillary. The migration time of the basic proteins using a persulfate initiator system was nearly identical to the azo-based initiator system based on an RSD of 1.1% (n=6), confirming a free radical-based coupling mechanism of the polymer to the silane.

EXAMPLE 21

The reproducibility of the coating process was studied by coating five capillaries in parallel with MET-PVP coating. The capillaries gave an RSD of less than 2.5% in migration times for the basic proteins and confirmed the reproducibility of the coating protocol.

EXAMPLE 22

Cationic coatings. In addition to attaching neutral polymers, the above coupling process was found suitable for attaching cationic polymers to the capillary surface as shown in Example 6. The cationic polymer coated capillary had an EO flow directed toward the anode. Separation of acidic proteins with average efficiencies of >200,000 plates/50 cm was accomplished using a cationic polymer coated capillary and 25 mM phosphate buffer at pH 7 (FIG. 4). FIG. 4 shows acidic protein separations using a cationic polymer coated capillary. Capillary: 50 cm total length: 45 cm to detector, 50 μm i.d. Buffer: 25 mM sodium phosphate at pH 7. Conditions: 20 kV (400 V/cm); Gravity Injection: 50 mm×10 s. Detection: UV, 210 nm. Sample concentration: 100 μg/ml. Peak identification (1) α-Lactalbumin (Bovine Milk), (2) Carbonic anhydrase (Bovine Erythrocytes), (3) Myoglobin (Horse Skeletal Muscle). Fast separations of acidic proteins were possible since the anionic proteins migrated with the EO flow.

EXAMPLE 23

The capillary was also useful in separating a standard mixture of seven inorganic anions (FIG. 5). FIG. 5 shows separation of test anions using a cationic polymer coated capillary. Capillary: 50 cm total length; 45 cm to detector, 50 μm i.d. Buffer: 1.6 mM Triethanolamine, 2.25 mM pyromellitic acid adjusted to pH 7.7 with 1N NaOH. Conditions: −20 kV (400 V/cm); Gravity Injection: 100 mm ×30 s. Detection: Indirect V, 250 nm. Sample concentration: 1 μg/ml. Peak identification: (1) Bromide, (2) Chloride, (3) Sulfate, (4) Nitrite, (5) Nitrate, (6) Fluoride, (7) Phosphate.

The seven ions were baseline resolved using a pyromellitic acid containing buffer with efficiencies ranging from 30,000 plates/50 cm for fluoride to 140,000 plates/50 cm for nitrate. Analysis of the same ions using fused silica capillaries and indirect UV detection required special additives coupled with special pretreatment steps to achieve flow reversal in the anodic direction.

EXAMPLE 24

Coupling mechanism. The following solution phase and CE experiments were performed to understand the mechanism of coupling the polymer to the silane.

CE Experiments. Several capillaries were coated under various conditions (Table II) using a 4% PVP polymer (MW 360K). Only the silane treated capillaries coated in the presence of the polymer, initiators and a thermal treatment were stable, suggesting a covalent attachment of the polymer to the MET silane through a hydrogen abstraction mechanism.

TABLE II

Effect of Capillary Coating Format on Stability

| Polymer Coating | Stability at pH 8 |
|---|---|
| Fused silica treated with 4% PVP 360K polymer and initiators followed by thermal treatment for 18 h at 80° C. | Not stable |
| Silanized capillary treated with 4% PVP 360K polymer at room temperature | Not stable |
| Silanized capillary treated with 4% PVP 360K polymer and thermal treatment for 18 h at 80° C. | Not stable |
| Silanized capillary treated with 4% PVP 360K polymer, initiators at room temperature | Not stable |
| Silanized capillary treated with 4% PVP 360K polymer, initiators and thermal treatment for 18 h at 80° C. | Stable and Generated Reproducible EO flow |

Literature on grafting vinyl[28] silanes and vinyl monomers[29] into polymer chains supports the covalent linkage of the polymer to the silane through double bonds on the silane. Similarly, linkage of the polymer to the silane through free radical sites created by hydrogen abstraction on other sites such as a α-carbon atom adjacent to the double bond is also possible.[30,31] Solution phase experiments were conducted to gain better understanding of the coupling mechanism.

EXAMPLE 25

Solution phase experiments. Various polymer solutions were prepared in the presence and absence of the added silane, and monitored after 18 h. The results are shown in Table III.

TABLE III

Solution Phase Experiments

| Mixture | Physical Appearance | Viscosity |
|---|---|---|
| PVP 2% (360K) in water | Clear | Low, 6 centipoise |
| PVP 2% (360K) in water + initiators @ RT | Clear | Low, 6 centipoise |
| PVP 2% (360K) in water + initiators @ 80° C. | Clear but with slight yellowish coloration | Low, 7 centipoise |
| PVP 2% (360K) in water + initiators + 1% methacryloxypropyl trimethoxy silane @ 80% | Turbid milky material showing gelation; bottom of flask shows increased gel attachment | High (>1000's of centipoise) |
| PVP 2% (360K) in water + initiators + 5% methacryloxypropyl trimethoxy silane @ 80% | Milky material; turbidity increases with excessive gelation; flask bottom shows excessive attachment of gel; precipitated material also interspersed in gel | Higher than previous sample |
| 1% methacryloxypropyl trimethoxy silane + initiators @ 80° C. | Turbid/milky water-like material with precipitated particulate material attached to bottom of flask | Similar to water |
| PVP 2% (360K) in acetic acid + initiators + 1% methacryloxypropyl trimethoxy silane @ 80° C. | Turbid low viscosity material; appears as latex phase; some spotting in bottom of flask; no gelation | 10 centipose viscosity |

PVP in the presence of silane and initiators when heated at 80° C. showed gelation and high viscosity, indicating cross-linking of the polymeric material. Several reactions occurred simultaneously: (1) homopolymerization of the silane through the vinyl groups, (2) the silane cross-linking with itself through condensation, (3) the silane cross-linking with the polymer, and (4) the polymer cross-linking with itself. Reaction (1) was minimal, as evidenced by no increase in viscosity when the silane was reacted with initiators in the absence of the polymer. Similarly, reaction (4) did not contribute to the huge increase in viscosity, since the polymer by itself showed a minimal increase in viscosity. Contribution of silane condensation to the viscosity of the matrix was expected to be minimal, based on the minimal increase in viscosity when the reaction was performed in acetic acid.

EXAMPLE 26

This was further tested by treating the materials obtained from the above experiment with sodium fluoride and NaOH. (See Table IV for results.)

TABLE IV

Effect of Alkali and Fluoride Treatment

| Mixture | Appearance |
|---|---|
| PVP 2% (360K) in water + initiators @ 80° C. | Clear; retained clarity after treatment with 1N NaOH |
| PVP 2% (360K) in water + initiators + 1% methacryloxypropyl trimethoxy silane @ 80° C. | Milky material; retained gel-like appearance after treatment with 1N NaOH (solution monitored at pH 12 and 13.2 for 1 week); gel-like appearance retained when 10% NaF was added and heated @ 50° C. for 18 h |
| PVP 2% (360K) in acetic acid + initiators + 1% methacryloxypropyl trimethoxy silane @ 80° C. | Milky material formed clear solution on treatment with 1N NaOH |
| methacryloxypropyl trimethoxy silane + initiators @ 80° C. | Turbid milky material; dissolved and formed clear solution when 1N NaOH was added. |

Treatment with fluoride ion is expected to inhibit silane condensation.[32] Similarly, extreme alkaline environment (above pH 10) inhibits silane condensation.[33] Treatment of the gel-like material (mixture of PVP, silane, initiator treated at 80° C.) with sodium fluoride and heating the mixture at 50° C. for 18 h showed no change in the solution. The retention of gel-like behavior by the PVP-silane mixture suggests a covalent cross-linking reaction between the polymer and the silane. Similarly, treating with 1N NaOH also showed no change in the PVP-silane mixture, further reaffirming the above result. The contribution from silane condensation to the huge increase in viscosity was minimal based on the results from NaOH treatment of the silane mixture and the PVP-silane mixture (in acetic acid). These results confirm that the silane cross-links with the polymer through a hydrogen abstraction mechanism.

EXAMPLE 27

We performed solution phase experiments, simulating coupling of PVP to an octylsilane by thermal treatment of PVP in the presence of an in-house synthesized trimethyldecylsilane reagent and initiators in dichloromethane solvent. A highly cross-linked gel-like material was formed at the bottom of the flask after the 18 hour thermal treatment step. PVP polymer with added initiators and PVP in the presence of trimethyldecylsilane with no added initiators did not form a gel-like material under the same conditions. Trimethyldecylsilane has no reactive functional groups for chemical coupling reactions. The above experiment suggests the formation of a covalent cross-link between PVP and timethyldecylsilane through a hydrogen abstraction mechanism.

EXAMPLE 28

Analysis of Milk Proteins. Separation of milk proteins (acidic proteins) became possible due to the low EO flow generated in the MET-PVP capillary. Published CE methods for analyzing milk proteins involve working at low buffer pH conditions with added polymer additives.[34] Due to the high pH stability of this coating, we attempted the above separations without adding any polymer additives at pH 8.4. Vitamin D milk was centrifuged at 8000 RPM for 4 minutes and incubated in a reduction buffer following a sample preparation procedure by Jong et al.[34] Excellent separation of the whey proteins from casein was achieved, as shown in FIG. 6. FIG. 6 shows separation of proteins from 2% Vitamin D Milk using a MET-PVP coated capillary. Capillary: 50 cm total length; 45 cm to detector; 50 μm i.d. Buffer: 100 mM sodium phosphate, pH 8.4 with 6M urea. Conditions: −30 kV (600 V/cm); Gravity Injection: 150 mm×30 s. Detection: UV, 210 nm. Peak identification: (1) α-Lactalbumin, (2) β-Lactoglobulin A & B, (3) α-Caseins (4) κ-Caseins. (5/6) β-Caseins.

Individual proteins were identified by running standard samples. These separations agreed well with the findings of Jong et al.[34] More than 50 runs were run in this capillary using various milk samples, and the capillary performed reliably, with no loss of separation efficiency.

EXAMPLE 29

Analysis of Hemoglobin variants. Baseline resolution of the four common variants of hemoglobin was achieved using a PVP-MET coated capillary with >650,000 plates/65-cm. The two commonly occurring normal hemoglobins are adult hemoglobin (HbA) and fetal hemoglobin (HbF). Sickle cell hemoglobin (HbS) is one of the abnormal hemoglobins, in which a single replacement of glutamic acid with valine occurs in position 6 of the beta chain, thus altering the solubility of this protein. In β-thalessemia HbC, the individual has lysine instead of glutamic acid in position 6 on their beta chain. More than 50 runs of these samples were run without any loss in separation efficiency or performance. The unidentified leading component was present in all the human Hb samples. These separations were far superior to those shown in the literature.[35]

REFERENCES (1) McCormick, R. M. *Anal. Chem.* 1988, 60 2322–2328
(2) Lauer, H. H.; McManigill, D. *Anal. Chem.* 1986, 58, 166–170
(3) *Encyclopedia of Polymer Science and Engineering*, John Wiley & Sons, New York, 1990, vol. 15, p.183
(4) Gordon, M. J.; Lee, K. J.; Arias, A. A.; Zare, R. N. *Anal. Chem.* 1991, 63, 69–72
(5) Bushey, M. M.; Jorgenson, J. W. *J. Chromatogr.* 1989, 480, 301–310
(6) Stover, F. S.; Haymore, B. L.; McBeth, R. J. *J. Chromatogr.* 1989, 470, 241–250
(7) Gilges M.; Kleemiss, M. H.; Schomburg, G. *Anal. Chem.* 1994, 66, 2038–2046
(8) Hjerten, S. *J. Chromatogr.* 1985, 347, 191–198
(9) Strege, M. A.; Lagu, A. L. *J. Chromatogr.* 1993, 630, 337–344
(10) Cifuentes, A.; de Frutos, M.; Santos, J. M.; Diez-Masa, J. C. *J. Chromatogr.* 1993, 655, 63–72
(11) Herren, B. J.; Shafer, S. G.; Van Alstine, J.; Harris, J. M.; Snyder, R. S. *J. Colloid Interface Sci.* 1987, 46–55
(12) Yalpani, M.; Brooks, D. E. *J. Polymer Sci.* 1985, 23, 1395–1405
(13) Harris, J. M.; Struck, E. C.; Case, M. G.; Paley, S.; Yalpani, M.; Van Alstine, J. M.; Brooks, D. E. *J. Polymer Sci.* 1984, 22, 341–352
(14) Hjerten, S.; Kubo, K. *Electrophoresis*, 1993, 14, 390–395
(15) Malik, A.; Zhao, Z.; Lee, M. L. *J. Microcol.* 1993, 5, 119–125
(16) Zhao, Z.; Malik, A.; Lee, M. L. *Anal. Chem.* 1993, 65, 2747–2752
(17) Cobb, K. A.; Dolnik, V.; Novotny, M. *Anal. Chem.* 1990, 62, 2478–2483
(18) Chiari, M.; Nesi, M.; Sandoval, J. E.; Pesek, J. J. *J. Chromatogr.* 1995, 717, 1–13
(19) Smith, J. T.; Rassi, Z. E. *Electrophoresis*, 1993, 14, 396–406
(20) Huang, M.; Plocek, J.; Novotny, M. V. *Electrophoresis*, 1995, 16, 396–401
(21) Schmalzing, D.; Piggee, C. A.; Foret, F.; Carrilho, E.; Karger, B. L. *J. Chromatogr.*, 1993, A 652, 149–159
(22) Odian, G. *Principles of Polymerization*, John Wiley & Sons, New York, 1991, p.249–255.
(23) *Encyclopedia of Polymer Science and Engineering*, Vol. 17, p.212
(24) Bulletin from GAF Chemicals, p.9
(25) Henglein, A. *J. Phys. Chem.*, 1959, 63, 1852–1858
(26) Anderson, C. C.; Rodriguez, F.; Thurston, D. A. *J. App. Polymer Sci.*, 1979, 23, 2453–2462
(27) *acrylamide Polymerization—A Practical Approach*, Biorad Bulletin 1156, 1987, p.3
(28) *Encyclopedia of Polymer Science and Engineering*, Vol. 17, p.833
(29) Lenz, R. W. *Organic Chemistry of Synthetic High Polymers*, John Wiley & Sons, New York, 1967, p.711–713
(30) *Encyclopedia of Polymer Science and Engineering*, Vol. 4, p.380
(31) Lenz, R. W. *Organic Chemistry of Synthetic High Polymers*, John Wiley & Sons, New York, 1967, P.292–293
(32) Greene, T. W.; Wuts, P. G. M. *Protective Groups in Organic Synthesis*, John Wiley & Sons, New York, 1991, p.68–86
(33) *Encyclopedia of Polymer Science and Engineering*, Vol. 15, p.184
(34) Jong, N.; Visser, S. Olieman *J. Chromatogr.* 1993, A 652, 207–213
(35) Chen, F.; Liu, C.; Hsieh, Y.; Sternberg, J. C. *Clin. Chem.* 1991, 37, 14–19

What is claimed is:

1. A method of coating a solid support surface which alters the properties of the support surface for separating soluble analytes in a fluid stream, said method comprising
   (a) covalently binding a coupling agent including functional groups, capable of forming free radicals under hydrogen extraction conditions in a layer on said support surface, and
   (b) thereafter, contacting said covalently bound coupling agent with a solution of said preformed polymer comprising totally saturated, substituted or unsubstituted carbon chain backbones including leaving groups under hydrogen abstraction conditions of elevated temperature in the presence of a free radical catalyst, said support surface being substantially insoluble in said solvent, to remove leaving groups from said preformed polymer carbon chain backbones to form free radical carbon binding sites and to convert at least some of said functional groups to free radicals thereby covalently bonding said free radical carbon binding sites to said coupling agent functional group free radicals and to crosslink at least some of said preformed polymer through thus-formed free radical carbon binding sites therein to form a three-dimensional polymer network coating on said solid support surface.

2. The method of claim 1 in which said preformed polymer leaving groups comprise halogens.

3. The method of claim 1 in which said preformed polymer leaving groups comprise hydrogen.

4. The method of claim 1 in which said coupling agent comprises at least one carbon chain with at least one leaving group.

5. The method of claim 4 in which at least part of said covalent bonding of said coupling agent to said preformed polymer is by leaving group abstraction from said coupling agent carbon chain.

6. The method of claim 1 in which said coupling agent layer comprises at least one carbon chain backbone with at least one unsaturated carbon to carbon linkage and at least a portion of said covalent bonding is by a free radical addition reaction between said one carbon to carbon linkage and said preformed polymer.

7. The method of claim 1 in which said support surface comprises silica and said coupling agent binds to said support surface through Si—O—Si linkages.

8. The method of claim 1 in which said preformed polymer is selected from the group consisting of PVP, polyacrylamide, polyethylene oxide and polyvinylalcohol.

9. The method of claim 1 in which said support surface comprises silica and said coupling agent comprises a silane.

10. The method of claim 1 in which said coupling agent is bound to said solid support surface by linkages selected from the group consisting of Si—C, Si—O—C, or Si—N.

11. The method of claim 1 in which at least some of said coupling agent is unbound in step (a) and said unbound coupling agent is removed from said solid support surface prior to step (b).

12. The method of claim 1 in which said coupling agent comprises a carbon chain and said leaving group comprises hydrogen which is abstracted from said carbon chain, and the covalent bonding of said coupling agent and preformed polymer is between hydrogen abstracted sites on said coupling agent and said preformed polymer.

13. The method of claim 1 in which said solid support surface comprises the inner wall of a fluid conduit.

14. The method of claim 13 in which said fluid conduit comprises a capillary suitable for capillary electrophoresis.

15. The method of claim 1 in which said solid support comprises the packing of a flowthrough particle bed.

16. The method of claim 1 in which said solid support surface is formed of a material selected from the group consisting of silica, quartz, glass, alumina, titanic, thoria, zirconia, and beryllia.

17. A method of coating a polymeric solid support surface with a surface having saturated or unsaturated carbon chains including leaving groups, said coating altering the properties of the support surface for separating components in a fluid stream, said method comprising contacting said support surface with preformed polymer comprising totally saturated carbon chain backbones under hydrogen abstraction conditions of elevated temperature in the presence of a free radical catalyst, to abstract hydrogen from said preformed polymer carbon chain backbones to form hydrogen abstracted carbon sites which covalently bond said support surface carbon chain backbones, and to crosslink at least some of said preformed polymer through hydrogen extraction carbon sites therein to form a three-dimensional polymer network coating on said solid support surface.

18. The method of claim 17 in which at least part of said covalent bonding is through said support surface carbon chains by hydrogen extraction therefrom.

19. The method of claim 17 in which said preformed polymer is formed by prepolymerizing a monomer including an unsaturated carbon-to-carbon linkage.

20. The method of claim 17 in which said preformed polymer is selected from the group consisting of PVP, polyacrylamide, polyethylene oxide and polyvinylalcohol.

21. The method of claim 17 in which the separation is by capillary electrophoresis and said conduit is a capillary.

22. The method of claim 17 in which hydrogen is abstracted from said support surface carbon chains and the bonding thereof with said preformed polymer is through hydrogen abstraction sites.

23. The method of claim 17 in which said solid support surface comprises the inner wall of a fluid conduit.

24. The method of claim 17 in which said fluid conduit comprises a capillary suitable for capillary electrophoresis.

25. The method of claim 17 in which said solid support comprises the packing of a flowthrough particle bed.

* * * * *

UNITED STATES PATENT AND TRADEMARK OFFICE
CERTIFICATE OF CORRECTION

PATENT NO. : 5,792,331
DATED : August 11, 1998
INVENTOR(S) : SRINIVASAN et al.

It is certified that error appears in the above-identified patent and that said Letters Patent is hereby corrected as shown below:

Column 6, line 17, delete "flunctionalities" and insert therefore --functionalities--.

Column 8, line 33, delete "a20" and insert therefore --azo--

Column 11, line 48, delete "Å" and insert therefore --A°--.

Column 15, line 31, delete "V, 210 nm." and insert therefore --UV, 210 nm.--.

Column 15, line 47, delete "Zhao et al. $^{6}$" and insert therefore --Zhao et al. $^{16}$--.

Column 16, line 34, delete "10-5" and insert therefore --$10^{-5}$".

Column 18, line 13, delete "V, 250 nm." and insert therefore --UV, 250 nm.--.

Signed and Sealed this

Tenth Day of August, 1999

Attest:

Q. TODD DICKINSON

*Attesting Officer*          *Acting Commissioner of Patents and Trademarks*

UNITED STATES PATENT AND TRADEMARK OFFICE
CERTIFICATE OF CORRECTION

PATENT NO. : 5,792,331
DATED : August 11, 1998
INVENTOR(S) : SRINIVASAN et al.

It is certified that error appears in the above-indentified patent and that said Letters Patent is hereby corrected as shown below:

On the title page, first column under [75] Inventors, delete "Neboisa" and insert therefore --Nebojsa--.

On the title page, second column 2, line 5, delete "Y-Radiation" and insert therefore --γ-Radiation--.

On the title page, second column, line 6, delete "Cappillary" and insert therefore -- Capillary--.

On the title page, second column, line 16, delete "Rotocol" and insert therefore -- Protocol--.

On page 2, first column, line 13, delete "Eliminatio" and insert therefore -- Elimination--.

On page 2, second column, line 14, delete "Y-Radiation" and insert therefore --γ-Radiation--.

Signed and Sealed this

Twenty-sixth Day of October, 1999

Attest:

Q. TODD DICKINSON

*Attesting Officer*  *Acting Commissioner of Patents and Trademarks*